(12) United States Patent
Hawkins et al.

(10) Patent No.: US 8,461,311 B2
(45) Date of Patent: Jun. 11, 2013

(54) TRAIL TRIMERS, METHODS AND USES THEREFOR

(75) Inventors: William G. Hawkins, Olivette, MO (US); Dirk Spitzer, Webster Groves, MO (US); Richard S. Hotchkiss, Chesterfield, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/155,577

(22) Filed: Jun. 8, 2011

(65) Prior Publication Data

US 2011/0300629 A1    Dec. 8, 2011

Related U.S. Application Data

(60) Provisional application No. 61/352,387, filed on Jun. 8, 2010.

(51) Int. Cl.
*C07K 14/52* (2006.01)
*C07K 14/47* (2006.01)
*C07K 16/46* (2006.01)

(52) U.S. Cl.
USPC ........... 530/402; 530/350; 530/300; 530/324; 530/387.3; 530/391.9; 514/18.9

(58) Field of Classification Search
None
See application file for complete search history.

(56) References Cited

U.S. PATENT DOCUMENTS

| 7,741,280 | B2 | 6/2010 | Guichard et al. |
| 2004/0014948 | A1 | 1/2004 | Halkier et al. |
| 2006/0154854 | A1 | 7/2006 | Russo-Marie et al. |
| 2007/0286843 | A1 | 12/2007 | Pfizenmaier et al. |
| 2008/0044376 | A1 | 2/2008 | Tur et al. |

FOREIGN PATENT DOCUMENTS

WO    WO 2005069726 A2 *   8/2005

OTHER PUBLICATIONS

Griffith et al., Induction and regulation of tumor necrosis factor-related apoptosis-inducing ligand/Apo-2 ligand mediated apoptosis in renal cell carcinoma, Canc. Res. 62:3093-3099, Jan. 2002.*
Rudikoff et al., Single amino acid substitution altering antigen-binding specificity, Proc. Nat. Acad. Sci. USA, 79:1979-1983, Mar. 1982.*
Yan et al., Two-amino acid molecular switch in an epithelial morphogen that regulates binding to two distinct receptors, Science, 290:523-527, Oct. 20, 2000.*
Zhou et al., The role of complement in the mechanism of action of rituximab for B-cell lymphoma: Implications for therapy, The Oncologist, 13:954-966, 2008.*

(Continued)

*Primary Examiner* — Claire Kaufman
(74) *Attorney, Agent, or Firm* — Zackson Law LLC; Saul L. Zackson

(57) ABSTRACT

Disclosed are TNF-related apoptosis-inducing ligand (TRAIL) trimers (TR3) and nucleic acids encoding covalently linked TRAIL trimers. A TRAIL trimer can have greater stability compared to native TRAIL, and can retain the native killing ability of TRAIL. Target specificity of a TR3 can be shown by blocking its activity with soluble death receptor 5 (DR5-Fc). Also disclosed are modified TRAIL trimers and nucleic. acids encoding them. These modifications include additional functional domains, such as antibody fragments (scFvs). A TR3 comprising an additional functional domain can allow for cell-specific delivery of the TR3. The inventors disclose TR3-decorated RBCs that target cell killing in a model of pancreatic cancer.

2 Claims, 19 Drawing Sheets

OTHER PUBLICATIONS

Harris et al., Coupling complement regulators to immunoglobulin domains generates effective anti-complement reagents with extended half-life in vivo, Clin. Exp. Immunol. 129:198-207, 2002.*

Ashkenazi, A., et al., "Ligand-based targeting of apoptosis in cancer: the potential of recombinant human apoptosis ligand 2/Tumor necrosis factor-related apoptosis-inducing ligand (rhApo2L/TRAIL)," J. Clin. Oncol. 2008, 26:3621-3630.

Bodmer, J.L., et al., "Cysteine 230 is essential for the structure and activity of the cytotoxic ligand TRAIL," J. Biol. Chem. 2000, 275:20632-20637.

Bremer, E., et al., "Target cell-restricted and -enhanced apoptosis induction by a scFv:sTRAIL fusion protein with specificity for the pancarcinoma-associated antigen EGP2," Int. J. Cancer 2004, 109:281-290.

Bremer, E., et al., "Targeted delivery of a designed sTRAIL mutant results in superior apoptotic activity towards EGFR-positive tumor cells," J. Mol. Med. 2008, 86:909-924.

Cha, S.S., et al., "2.8 A resolution crystal structure of human TRAIL, a cytokine with selective antitumor activity," Immunity 1999, 11:253-261.

Cha, S.S., et al., "Crystal structure of TRAIL-DR5 complex identifies a critical role of the unique frame insertion in conferring recognition specificity," J. Biol. Chem. 2000, 275:31171-31177.

Chowdhury, P.S., et al., "Isolation of a high-affinity stable single-chain Fv specific for mesothelin from DNA-immunized mice by phage display and construction of a recombinant immunotoxin with anti-tumor activity," Proc. Natl. Acad. Sci. U S A 1998, 95:669-674.

Chowdhury and Pastan, "Improving antibody affinity by mimicking somatic hypermutation in vitro," Nat. Biotechnol. 1999, 17:568-572.

Falschlehner C., et al., "TRAIL signalling: decisions between life and death," Int. J. Biochem. Cell Biol. 2007, 39: 1462-1475.

Garber, K., "New apoptosis drugs face critical test," Nat. Biotechnol. 23:409-411, 2005.

Griffith, T.S., et al., "TRAIL gene therapy: from preclinical development to clinical application," Curr. Gene Ther. 2009, 9:9-19.

Hymowitzz, S.G., et al., "Triggering cell death: the crystal structure of Apo2L/TRAIL in a complex with death receptor 5," Mol. Cell 1999, 4:563-571.

Kelley, R.F., et al., "Receptor-selective mutants of apoptosis-inducing ligand 2/tumor necrosis factor-related apoptosis-inducing ligand reveal a greater contribution of death receptor (DR) 5 than DR4 to apoptosis signaling," J. Biol. Chem. 2005, 280:2205-2212.

Kohlhaas, S.L., et al., "Receptor-mediated endocytosis is not required for tumor necrosis factor-related apoptosis-inducing ligand (TRAIL)-induced apoptosis," J. Biol. Chem. 282:12831-12841, 2007.

Krippner-Heidenreich, A., et al., "Single-chain TNF, a TNF derivative with enhanced stability and antitumoral activity," J. Immunol. 2008, 180:8176-8183.

LeBlanc, H.N., et al., "Apo2L/TRAIL and its death and decoy receptors," Cell Death Differ. 2003, 10:66-75.

McDunn, J.E., et al., "Peptide-mediated activation of Akt and extracellular regulated kinase signaling prevents lymphocyte apoptosis," FASEB J. 2008, 22:561-568.

Merino, D., et al., "TRAIL in cancer therapy: present and future challenges," Expert Opin. Ther. Targets 2007, 11: 1299-1314.

Mongkolsapaya, J., et al., "Structure of the TRAIL-DR5 complex reveals mechanisms conferring specificity in apoptotic initiation," Nat. Struct. Biol. 1999, 6:1048-1053.

Pitti, R.M., et al., "Induction of apoptosis by Apo-2 ligand, a new member of the tumor necrosis factor cytokine family," J. Biol. Chem. 1996, 271: 12687-12690.

Schneider et al., "Potent antitumoral activity of TRAIL through generation of tumor-targeted single-chain fusion proteins," Cell Death and Disease. 2010, 1(8):e68: 1-10.

Spencer, S.L., "Non-genetic origins of cell-to-cell variability in TRAIL-induced apoptosis," Nature 2009, 459:428-432.

Spitzer, D., et al., "ScFv-mediated in vivo targeting of DAF to erythrocytes inhibits lysis by complement," Mol. Immunol. 2004, 40:911-919.

Spitzer et al., "Properdin can initiate complement activation by binding specific target surfaces and providing a platform for de novo convertase assembly," J. Immunol. 2007, 179:2600-2608.

Ten, C.B., et al., "A novel AML-selective TRAIL fusion protein that is superior to Gemtuzumab Ozogamicin in terms of in vitro selectivity, activity and stability," Leukemia 2009, 23:1389-97.

Wiley, S.R., et al., "Identification and characterization of a new member of the TNF family that induces apoptosis," Immunity 1995, 3:673-682.

Zhang, H-G et al., "Hepatic DR5 induces apoptosis and limits adenovirus gene therapy product expression in the liver," J. Virol. 2002, 76: 5692-5700.

* cited by examiner

Secreted single chain TRAIL-6xHis

SEQUENCE LISTING

<160> NUMBER OF SEQ ID NOS: 4

<210> SEQ ID NO 1
<211> LENGTH: 169
<212> TYPE: PRT
<213> ORGANISM: Artificial Sequence
<220> FEATURE:
<223> OTHER INFORMATION: fragment of human TRAIL amino acids 114-281

<400> SEQUENCE: 1

```
Met Val Arg Glu Arg Gly Pro Gln Arg Val Ala Ala His Ile Thr Gly
 1               5                  10                  15

Thr Arg Gly Arg Ser Asn Thr Leu Ser Ser Pro Asn Ser Lys Asn Glu
            20                  25                  30

Lys Ala Leu Gly Arg Lys Ile Asn Ser Trp Glu Ser Ser Arg Ser Gly
        35                  40                  45

His Ser Phe Leu Ser Asn Leu His Leu Arg Asn Gly Glu Leu Val Ile
    50                  55                  60

His Glu Lys Gly Phe Tyr Tyr Ile Tyr Ser Gln Thr Tyr Phe Arg Phe
65                  70                  75                  80

Gln Glu Glu Ile Lys Glu Asn Thr Lys Asn Asp Lys Gln Met Val Gln
                85                  90                  95

Tyr Ile Tyr Lys Tyr Thr Ser Tyr Pro Asp Pro Ile Leu Leu Met Lys
            100                 105                 110

Ser Ala Arg Asn Ser Cys Trp Ser Lys Asp Ala Glu Tyr Gly Leu Tyr
        115                 120                 125

Ser Ile Tyr Gln Gly Gly Ile Phe Glu Leu Lys Glu Asn Asp Arg Ile
    130                 135                 140

Phe Val Ser Val Thr Asn Glu His Leu Ile Asp Met Asp His Glu Ala
145                 150                 155                 160

Ser Phe Phe Gly Ala Phe Leu Val Gly
                165
```

<210> SEQ ID NO 2
<211> LENGTH: 191
<212> TYPE: PRT
<213> ORGANISM: Artificial Sequence
<220> FEATURE:
<223> OTHER INFORMATION: fragment of human TRAIL amino acids 91-281

<400> SEQUENCE: 2

```
Met Ile Leu Arg Thr Ser Glu Glu Thr Ile Ser Thr Val Gln Glu Lys
 1               5                  10                  15

Gln Gln Asn Ile Ser Pro Leu Val Arg Glu Arg Gly Pro Gln Arg Val
            20                  25                  30

Ala Ala His Ile Thr Gly Thr Arg Gly Arg Ser Asn Thr Leu Ser Ser
        35                  40                  45

Pro Asn Ser Lys Asn Glu Lys Ala Leu Gly Arg Lys Ile Asn Ser Trp
    50                  55                  60

Glu Ser Ser Arg Ser Gly His Ser Phe Leu Ser Asn Leu His Leu Arg
65                  70                  75                  80

Asn Gly Glu Leu Val Ile His Glu Lys Gly Phe Tyr Tyr Ile Tyr Ser
                85                  90                  95

Gln Thr Tyr Phe Arg Phe Gln Glu Glu Ile Lys Glu Asn Thr Lys Asn
            100                 105                 110

Asp Lys Gln Met Val Gln Tyr Ile Tyr Lys Tyr Thr Ser Tyr Pro Asp
        115                 120                 125
```

-continued

```
Pro Ile Leu Leu Met Lys Ser Ala Arg Asn Ser Cys Trp Ser Lys Asp
    130                 135                 140

Ala Glu Tyr Gly Leu Tyr Ser Ile Tyr Gln Gly Gly Ile Phe Glu Leu
145                 150                 155                 160

Lys Glu Asn Asp Arg Ile Phe Val Ser Val Thr Asn Glu His Leu Ile
                165                 170                 175

Asp Met Asp His Glu Ala Ser Phe Phe Gly Ala Phe Leu Val Gly
            180                 185                 190

<210> SEQ ID NO 3
<211> LENGTH: 6
<212> TYPE: PRT
<213> ORGANISM: artificial
<220> FEATURE:
<223> OTHER INFORMATION: fragment of human TRAIL amino acids 108-113

<400> SEQUENCE: 3

Gln Asn Ile Ser Pro Leu
1               5

<210> SEQ ID NO 4
<211> LENGTH: 23
<212> TYPE: PRT
<213> ORGANISM: Artificial Sequence
<220> FEATURE:
<223> OTHER INFORMATION: fragment of human TRAIL amino acids 91-113

<400> SEQUENCE: 4

Met Ile Leu Arg Thr Ser Glu Glu Thr Ile Ser Thr Val Gln Glu Lys
1               5                   10                  15

Gln Gln Asn Ile Ser Pro Leu
            20
```

TRAIL TRIMERS, METHODS AND USES THEREFOR

CROSS REFERENCE TO RELATED APPLICATIONS

This application claims priority from U.S. Provisional Application Ser. No. 61/352,387, filed Jun. 8, 2010, which is incorporated herein by reference in its entirety.

GOVERNMENT SUPPORT

This work received support from NIH grants 5P30CA9184208 and 1R21CA150945. The government may have certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

The extrinsic cell death pathway is triggered by ligand-receptor interactions that lead to intracellular signaling events, which ultimately result in the death of the target cell (apoptosis). One such ligand is represented by a member of the tumor necrosis factor (TNF) superfamily, TNF-related apoptosis-inducing ligand (TRAIL or Apo2L; Wiley, S. R., et al., Immunity 1995, 3:673-682; Pitti, R. M., et al., J. Biol. Chem. 1996, 271: 12687-12690). TRAIL-based therapeutics have been shown to be more effective inducers of apoptosis in cancer cells than in normal cells (Falschlehner C., et al., Int. J. Biochem. Cell Biol. 2007, 39: 1462-1475. Endogenous TRAIL exists as a homotrimer, a critical requirement for its biological function. Various expression systems have been explored, and much progress has been made to obtain biologically active TRAIL proteins such as nontagged and tagged (FLAG, His, etc., with or without tag-mediated crosslinking), inclusion of trimerization domains such as a leucine zipper and/or an isoleucine zipper, and stabilization of the trimers with cations (i.e., zinc; Merino, D., et al., Expert Opin. Ther. Targets 2007, 11: 1299-1314). In all previous reports, the building block for trimeric, recombinant TRAIL has been expressed from monomer-encoding cDNA sequences and has required self-association into functionally active trimers.

SUMMARY

The present inventors disclose covalently linked TRAIL trimers (TR3) and nucleic acids encoding covalently linked TRAIL trimers. In various configurations, a TRAIL trimer of the present teachings can have greater stability compared to native TRAIL, and can retain the native killing ability of TRAIL. In some configurations, target specificity of a TR3 can be shown by blocking its activity with soluble death receptor 5 (DR5-Fc). In addition, the inventors disclose modified TRAIL trimers and nucleic acids encoding them. In various embodiments, these modifications can include additional functional domains, such as antibody fragments (scFvs). In some configurations, a modified TR3 such as a TR3 comprising an additional functional domain can allow for cell-specific delivery of the TR3. In some configurations, a modification such as the addition of a functional domain can be stoichiometrically controlled. In some configurations, a modification can be inconsequential with regard to the bioactivity of TRAIL. In various embodiments, a TR3, including a modified TR3, can be a cancer-selective drug. In some configurations, a TR3 that comprises an additional biologically active moiety such as a functional domain of a protein can have fewer off-target toxicities compared to TRAIL alone. In some configurations, a TR3 that comprises an additional biologically active moiety such as a functional domain of a protein can have enhanced killing capacities compared to the moiety alone. In some aspects, TR3 activity can be targeted to an RBC membrane. The inventors disclose TR3-decorated RBCs that target cell killing in a model of pancreatic cancer.

In various embodiments, a trimer of a TNF-related apoptosis-inducing ligand (TRAIL) can comprise, consist of, or consist essentially of three consecutive extracellular TRAIL domains fused together in a head-to-tail configuration. A trimer consisting essentially of three consecutive extracellular TRAIL domains fused together in a head-to-tail configuration can further comprise additional amino acids, conservative substitutions, as well as non-amino acid moieties such as a label (e.g., a fluorophor or a radionuclide). In various configurations, a trimer of the present teachings can comprise TRAIL domains in which each domain comprises a sequence having at least 99% identity with SEQ ID NO: 1. In various embodiments, a trimer of the present teachings can further comprise a cell-targeting domain, such as, without limitation, an antibody fragment. An antibody fragment can be, for example, an scFv. In various embodiments, a trimer of the present teachings can further comprise a spacer between the cell-targeting domain and the TRAIL domains. A spacer can be, for example, an amino acid sequence comprising a plurality of short consensus repeats (SCRs), for example 4 short consensus repeats. In some configurations, a spacer can comprise globular domains of human complement regulatory proteins decay accelerating factor (DAF, CD55) and complement receptor 1 (CR1, CD35). In some configurations, a spacer can comprise four SCRs and globular domains of the human complement regulatory proteins decay accelerating factor (DAF, CD55) and complement receptor 1 (CR1, CD35). In various configurations, a TRAIL trimer can also further comprise a signal peptide sequence.

In some embodiments, the inventors disclose anticancer therapeutics. An anticancer therapeutic of these embodiments can comprise a TRAIL trimer described herein.

In some embodiments, the inventors disclose nucleic acids comprising a sequence encoding a TRAIL trimer.

In various configurations, a nucleic acid comprising a sequence encoding a TRAIL trimer can be comprised by a vector, such as, for example, a plasmid or a virus. In some configurations, a nucleic acid sequence of the present teachings can further comprise a sequence encoding a signal peptide.

The inventors also disclose methods of inducing apoptosis in a tumor cells. In various embodiments, these methods comprise contacting a cell such as a cancerous tumor cell with a TRAIL trimer described herein, including, without limitation, a TRAIL trimer comprising a targeting moiety. A cancerous tumor cell which can be subject to apoptotic death upon contact with a TRAIL trimer of the present teachings can be, for example, a pancreatic cancer cell.

DETAILED DESCRIPTION

Figure 1:
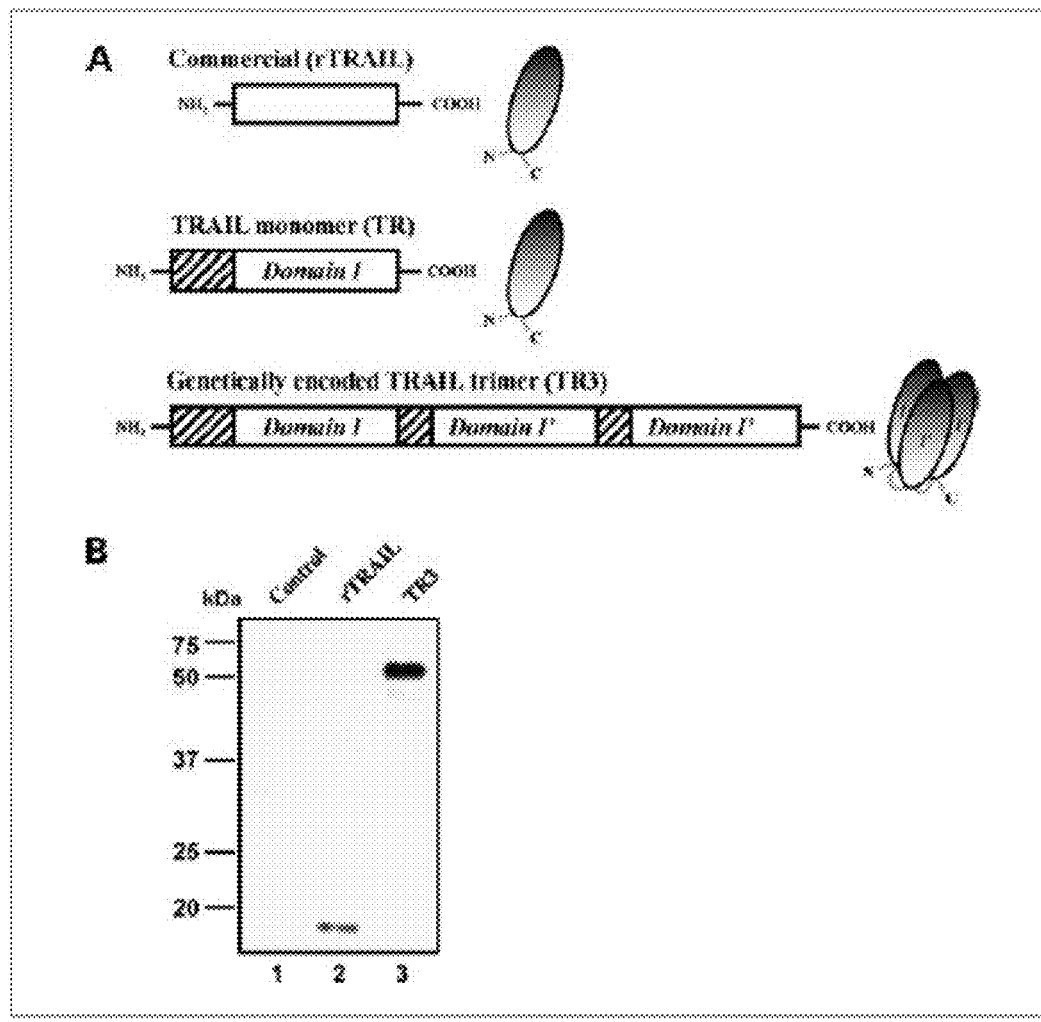
FIG. 1A illustuates a schematic representation of the TRAIL forms used.
FIG. 1B illustrates a Western blot analysis of commercially available rTRAIL.

The present inventors have developed TRAIL trimers (TR3), and TRAIL trimer expression constructs. Additional modifications show its utility as an investigative tool and as a platform on which to build cell-targeted anticancer therapeutics. The inventors also present methods to generate recombinant human TRAIL (TR3-family). These methods are based on a single polypeptide format featuring potent apoptosis-inducing activity and enhanced stability. In some configurations, TR3 can be further modified in a stoichiometrically controlled fashion without interfering with TRAIL function. As a consequence, in various configurations, the resulting multidomain therapeutic can have greater affinity for a tumor and a reduced affinity toward normal host cells. In some configurations, some advantages can include stronger and more sustained induction of the death receptor pathway in targeted tumor cells. In some embodiments, a tumor-targeted TR3 can enhance the effectiveness of other chemotherapies while limiting off-target toxicities to a patient. This work discloses (1) trimerization of a death signal and (2) incorporation of a covalently linked targeting domain with additional specificity for an overexpressed tumor antigen. Our results with the RBC-targeted TR3 construct represent the first demonstration that the apoptogenic plateau of TRAIL has been brought close to 100%. This strategy can increase the potency of a TRAIL-based treatment regimen itself and can integrate with standard therapies, further increasing their efficacy and reducing toxicity.

The present inventors conceive a multitude of potential different effects on target cell killing:

The various TR3 forms can have an overall difference in tumor cell killing capacity, e.g. following a 24 h incubation time. Such an effect can be evident by differences in absolute cell counts, i.e. cell viability, which can be determined by standard assays.

The present inventors also disclose dual-domain therapeutics. A dual-domain therapeutic of the present teachings can comprise, for example, a mesothelin targeting epitope (scFv) and a covalently linked TRAIL trimer (TR3). A dual domain therapeutic of the present teachings can be active against a panel of human pancreatic cancer cell lines in vitro and in some embodiments can be used to elaborate mechanistic details regarding the role of tumor cell tethering in therapeutic activity. In various configurations, the scFv(hM-L)-TR3 fusion protein can both bind to mesothelin on pancreas cancer cells and induce DR4/5-mediated apoptosis.

The present inventors also disclose that a membrane-immobilized form of TR3 (attached to the surface of mouse RBCs in analogy to a nanoparticle) can be capable of killing tumor cells. In some embodiments, a TR3 molecule can be attached to a target cell via antibody recognition of a tumor-associated antigen. In some configurations, a tumor can be a pancreas tumor and a tumor-associated antigen can be mesothelin. Nearly all human pancreatic tumors express increased amounts of mesothelin on their surface and we show that human pancreatic tumor cell lines express abundant mesothelin. In addition, we demonstrate that these cell lines are differentially sensitive to TRAIL-mediated killing. In some configurations, our scFv-TR3 construct can accumulate on tumor cell surfaces and can be available to sample multiple TRAIL receptors thereby increasing the likelihood for triggering apoptosis via DR4 and/or DR5. The present inventors also describe the use of a generic expression cassette that allows fusion of additional bioactive modifications onto an initial drug platform (TR3). The inventors demonstrate how such modifications can confer additional properties onto TR3, including the ability to be specifically delivered to an antigen-defined target cell, while retaining the biologic activity of TRAIL.

The data show that the function of each domain of precursor fusion proteins scFv(hM-L)-hDAF and scFv(mR)-S-TR3 is maintained in the N-terminal scFv, C-terminal effector arm arrangement. Therefore the combination of an N-terminal scFv(hM-L) domain and a C-terminal TR3 domain should exhibit both biologic activities. In addition, in vivo activity can be tested in a subcutaneous (s.c.) xenogeneic tumor implant model using patient-derived pancreatic cancer cell lines engineered to express firefly luciferase.

Figure 8:
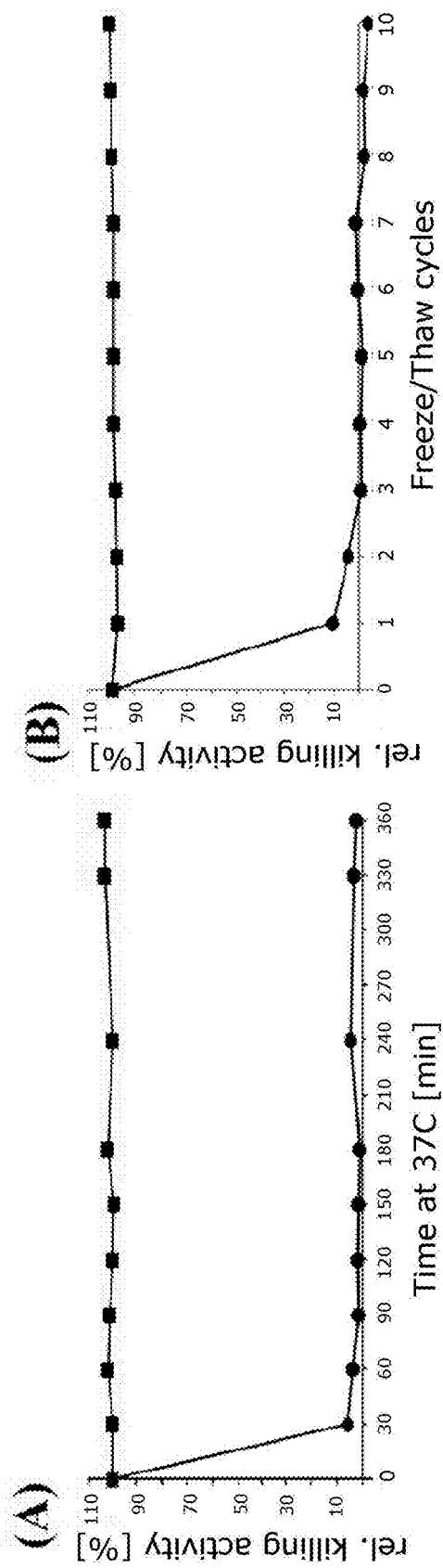
FIG. 8A illustrates killing capacity of TR3 and rTRAIL at 37° C.
FIG. 8B illustrates killing capacity of TR3 and rTRAIL following 10 freeze/thaw cycles.

The present inventors further disclose a TR3 containing a 6× histidine tag (TR3-6×His). This can be generated by standard cloning techniques (Sambrook, J., et al., Molecular Cloning: A Laboratory Manual, 3rd ed. Cold Spring Harbor Laboratory Press, Cold Spring Harbor, N.Y., 2001). The present inventors have found that the epitope tag can be placed at various positions within a polypeptide such as a TR3 molecule (FIG. 8, at the N- and C-terminus, and at the domain-I/II and -II/III junctions) without destroying function.

In some embodiments, the inventors disclose a mesothelin-targeted TR3 form. Mechanistically, the inventors' approach differs fundamentally from the RBC-mediated tumor cell killing (exclusively bystander or cell contact-dependent), since TR3 can be attached to the cancer cell itself. In some configurations, the mesothelin-specific TR3 constructs can kill the same cells they are targeting. In addition, a bystander effect can also be at work, similar to what we observed for the RBC-mediated tumor cell killing, when the drug binds via scFv to one cell and exerts killing via TR3-DR interaction with a neighboring cell.

In some configurations, a TRAIL trimer can comprise a spacer that has advantages over a spacer-deficient analog. For example, a spacer-containing scFv(hM)-S-TR3 form can have advantageous properties over its spacer-deficient shorter analog. Without being limited by theory, these properties may be due to its elongated structure. In addition, because of the nature of the expression cassette, the domain architecture in the spacer region of our construct can be changed. By increasing spacer length or introducing more flexible spacer domains such as those used by our group (McDunn, J. E., et al., FASEB J. 2008, 22:561-568), we can determine whether the activity of the original construct can be limited by geometrical constraints.

In some embodiments, a trimer of the present teachings can include a MMP-9 cleavage site upstream of the TR3 trimer (i.e. between the targeting/spacer domain and TR3 [scFv-S-MMP9-TR3]) to allow the TR3 portion of the fusion protein to being released from the tumor cell surface and now available to engage the death receptors.

To demonstrate applicability of mesothelin-targeted TR3 in vivo, we can engraft BxPC3 and other pancreas cancer cell lines (including CFPAC and possibly patient-derived cell lines) in our nude mouse model. In order to monitor tumor growth quantitatively, we can perform non-invasive whole body live animal scans employing the Luciferase system. Consequently, we can genetically modify our newly established pancreatic cancer cell lines to express the Firefly Luciferase cDNA. We have multiple expression plasmids that contain either both a selection marker (G418, Neomycin) and the Luciferase cDNA in one vector (pMSLIN; Spitzer, D., et al., Hum. Gene Ther. 1999, 10:1893-1902) or a Luciferase-eGFP fusion gene (pTLUEG), We have previously had success using the manufacturer's recommended settings for nucleofection of pancreas cancer cells (amaxa system) and stable cell pools can be generated by G418 selection. Enrichment for high GIP-expressing cell pools can be accomplished with FACS sorting. Luciferase expression can be verified by luciferin luminescence. These luciferase-expressing tumor cell lines can then be used in our xenogeneic tumor models. Daily during and after the treatment interval and at least twice weekly during establishment of the tumors, tumor size can be determined by measuring luciferase activity as described below.

The stably luciferase-expressing pancreatic cancer cell lines can be injected subcutaneously and orthotopically into our nude mice. Four to six weeks post-inoculation, we expect to obtain tumor formation of about 5-6 mm in size. During this initial phase, tumor development can be monitored quantitatively following intraperitoneal (i.p.) injection of Luciferin substrate (~3 mg/animal) via live animal scan at various time points post-tumor challenge (depending in the tumor inoculation modus).

Treatment shortly following tumor injection: In this minimal residual disease model, the mice can receive, e.g. the Mesothelin-targeted TRAIL form scFv(hM)-S-TR3 via the i.p. and/or i.v. route several days post-tumor cell injection.

Treatment of established tumors: This modification of the above protocol can more closely mimic the situation found in pancreatic cancer patients where surgical resection is not an option. The only difference here is the timing of treatment relative to tumor cell implantation. Tumors can be allowed to form and at a size of 5-6 mm treatment can be initiated. In some embodiments, a daily dosing regimen of about 1 mg/kg can achieve its therapeutic window. In some configurations, treatment can occur over a week-long interval. Survival experiments can proceed until at least 50% of mice have succumbed to their tumor. Surrogate end points for death can include tumor diameter>10 mm, if an individual mouse is obviously distressed and suffering, or exhibits tumor ulceration. Combination therapies can be tested by adding either irradiation or gemcitabine treatment according to the dosing regimens we recently developed (Kashiwagi, et al., J. Transl. Med. 2009, 7:24).

Figure 15:
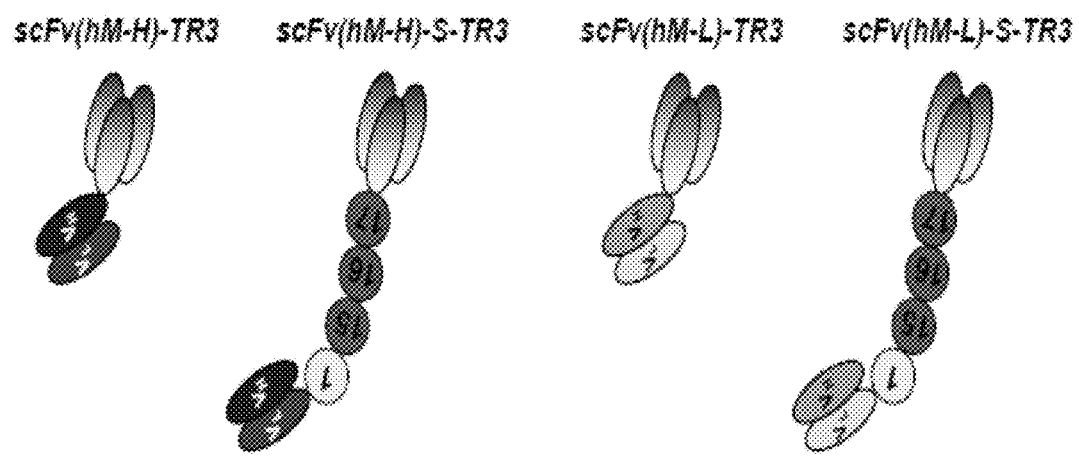
FIG. 15 illustrates mesothelin-targeted TR3 forms.

Antibodies and scFvs are known to exhibit varying affinities for a given antigen. We are able to study anti-human Mesothelin scFvs with High and Low affinity (H and L). As described above (FIG. 13), we already verified the binding capacity of scFv-SS toward human Mesothelin. This scFv has been described (Chowdhury, P. S., et al., Proc. Natl. Acad. Sci. USA 1998, 95:669-674) and represents a low affinity antibody fragment [scFv(hM-L)], which can be increased by somatic hypermutation in vitro (Chowdhury and Pastan, Nat. Biotechnol. 1999, 17:568-572) (FIG. 15, right panel). In this study, the authors identified two amino acid substitutions within the scFv-SS sequence (CDR-L3) that led to a 15-fold increase in binding affinity over the parental antibody fragment, designated scFv-SS1, corresponding to scFv(hM-H) (FIG. 15, left panel). These two substitutions are located at positions 93/94 in which a Gly/Tyr motif is replaced by a Lys/His sequence. These alterations can be introduced by standard methods (site-directed mutagenesis) and the impact of the increased binding affinity of the targeting domain can be studied on Mesothelin-positive BxPC3 cells in vitro.

Since we have already shown on multiple occasions that the different TR3 extensions have essentially no impact on TR3 function, we can measure the relative apoptosis that the different TRAIL constructs induce on Jurkat cells. Because Jurkat cells lack any mesothelin expression, target cell apoptosis may be mediated only via TR3:DR5 interaction. The impact of the N-terminal extensions, i.e., the role of the scFv: Mesothelin interaction can be considered negligible. Based on these results, we can identify the amount of each scFv (hM)-TR3 construct required to kill a constant number of Jurkat target cells. Target cell killing can be determined by different means such as caspase activation, TUNEL staining, annexin-V/PI staining and/or 7-AAD/PI staining or cell viability assays (e.g., MTT, CellTiter-Glo [Promega]). We can also perform the same experiments with Mesothelin-targeted TR3 but can also block the putative binding site(s) with the respective scFv(hM-H or L)-DAF fusion protein as described in FIG. 13.

To enforce bioactive trimerization of recombinant TRAIL, the present inventors have developed a strategy that does not depend on the spontaneous association of individual monomers. Endogenous human TRAIL is initially synthesized as a Type-II transmembrane protein with its carboxyl (C)-terminus facing the extracellular milieu. It is subsequently cleaved at amino acid (aa) position V114 and is then released from the cell surface (aa 114-281). The majority of recombinant secreted human TRAIL forms generated to date are comprised of amino acid 114-281 or contain a slightly elongated amino (N)-terminus (aa 95-281).

Comparative functional studies were performed using tissue culture supernatants from transiently transfected HEK293T cells as described above but this time, the concentration process was omitted. We found that all the extra domains tested in this study fused to the N-terminus of TR3 (eGFP-, scFv-, and scFv-S-) had a negligible effect on the fluid phase killing activity employing the Jurkat reporter cell assay (data not shown), In fact, we have already replaced the targeting domain of scFv(mR)-TR3 with an analog that recognizes human RBCs (scFv[hR]-TR3) and could demonstrate unaltered killing characteristics (not shown).

In some embodiments, the targeting domain of scFv(mR)-S-TR3 and scFv(mR)-TR3 (against mouse RBCs) can be exchanged with a scFv with specificity for human Mesothelin (scFv(hM)-S-TR3 and scFv(hM)-TR3). Since the sequence information of such a targeting vehicle (scFv-SS; Chowdhury, P. S., et al., Proc. Natl. Acad. Sci. USA 1998, 95:669-674) was publicly available (NCBI, AF035617), we had the cDNA of scFv-SS commercially synthesized (GenScript). Of note, the binding epitope of scFv-SS has been localized to the membrane-associated, GPI-linked mature form of human Mesothelin. We generated a fusion protein comprised of scFv-SS with a soluble form of the human complement regulator DAF, designed solely to function as a protein tag (Spitzer, D., et al., Mol. Immunol. 2004, 40:911-919).

Our data demonstrate that a membrane-immobilized form of TR3 (attached to the surface of mouse RBCs in analogy to a nanoparticle) can kill tumor cells (via a cell contact-dependent mechanism). The present inventors disclose targeting a TR3 molecule to a target cell via antibody recognition. In these embodiments, the inventors disclose attaching a TR3 molecule to a target cell via antibody recognition, such as, for example, by using antibody recognition of the pancreas tumor-associated antigen mesothelin. Nearly all human pancreatic tumors express increased amounts of mesothelin on their surface; the inventors show that human pancreatic tumor cell lines express abundant mesothelin. In addition, we have preliminary data which demonstrate that these cell lines are differentially sensitive to TRAIL-mediated killing. In some configurations, our scFv-TR3 construct can accumulate on tumor cell surfaces and can be available to sample multiple TRAIL receptors thereby increasing the likelihood for triggering apoptosis via DR4 and/or DR5.

TNF-related apoptosis inducing ligand (TRAIL, Apo2L) has been shown to exhibit potent apoptotic activity against tumor cells with lower toxicity to nontransformed cells (Falschlehner, C., et al., Int. J. Biochem. Cell Biol. 39:1462-1475, 2007). This makes it an exciting drug candidate as a tumor therapeutic. In fact, recombinant TRAIL is currently being evaluated by multiple pharmaceutical companies in numerous clinical trials (Garber, K., Nat. Biotechnol. 23:409-411, 2005). The molecule naturally exists as a homotrimer in vivo and is internalized upon death receptor interaction (Kohlhaas, S. L., et al., J. Biol. Chem. 282:12831-12841, 2007). However, the same authors report that receptor internalization is not required for TRAIL to cause apoptosis. TRAIL can be produced recombinantly in various expression systems and much progress has been made to obtain biologically active protein. Originally, recombinant TRAIL was generated by simply expressing those amino acids that are present in the native, secreted protein. Due to the intrinsic tendency of the monomers to aggregate into functionally active trimers, apoptosis-inducing molecules can be obtained.

However, the activity of recombinant TRAIL is crucially dependent on this trimerization and numerous specific designs of recombinant TRAIL have been made (non-tagged, tagged [FLAG, His, etc., with or without tag-mediated crosslinking], inclusion of trimerization domains such as a leucine zipper [LZ] and/or an isoleucine zipper [ILZ], and stabilization of the trimers with cations [i.e., Zinc]) (Merino, D., et al., Expert Opin. Ther. Targets 11:1299-1314, 2007). In all cases reported to date, the building block for trimeric, recombinant TRAIL is expressed from monomer-encoding cDNA sequences and requires self association into functionally active trimers.

In some embodiments, the present inventors demonstrate adding functionality to the TR3 molecule without altering its biologic activity. Their example demonstrates the generality of the approach to modifying TNF-superfaimly ligands for both research and therapeutic use.

The inventors disclose a TR3 construct which increases the stability of the existing cancer drug TRAIL. They also extending the functionality of TR3 using a generic expression cassette that allows fusion of additional bioactive modifications onto the initial drug platform (TR3) and further demonstrate how these modifications can confer additional desired properties onto TR3, including the ability to be specifically delivered to an antigen-defined target cell, while retaining the biologic activity of TRAIL.

Figure 7:
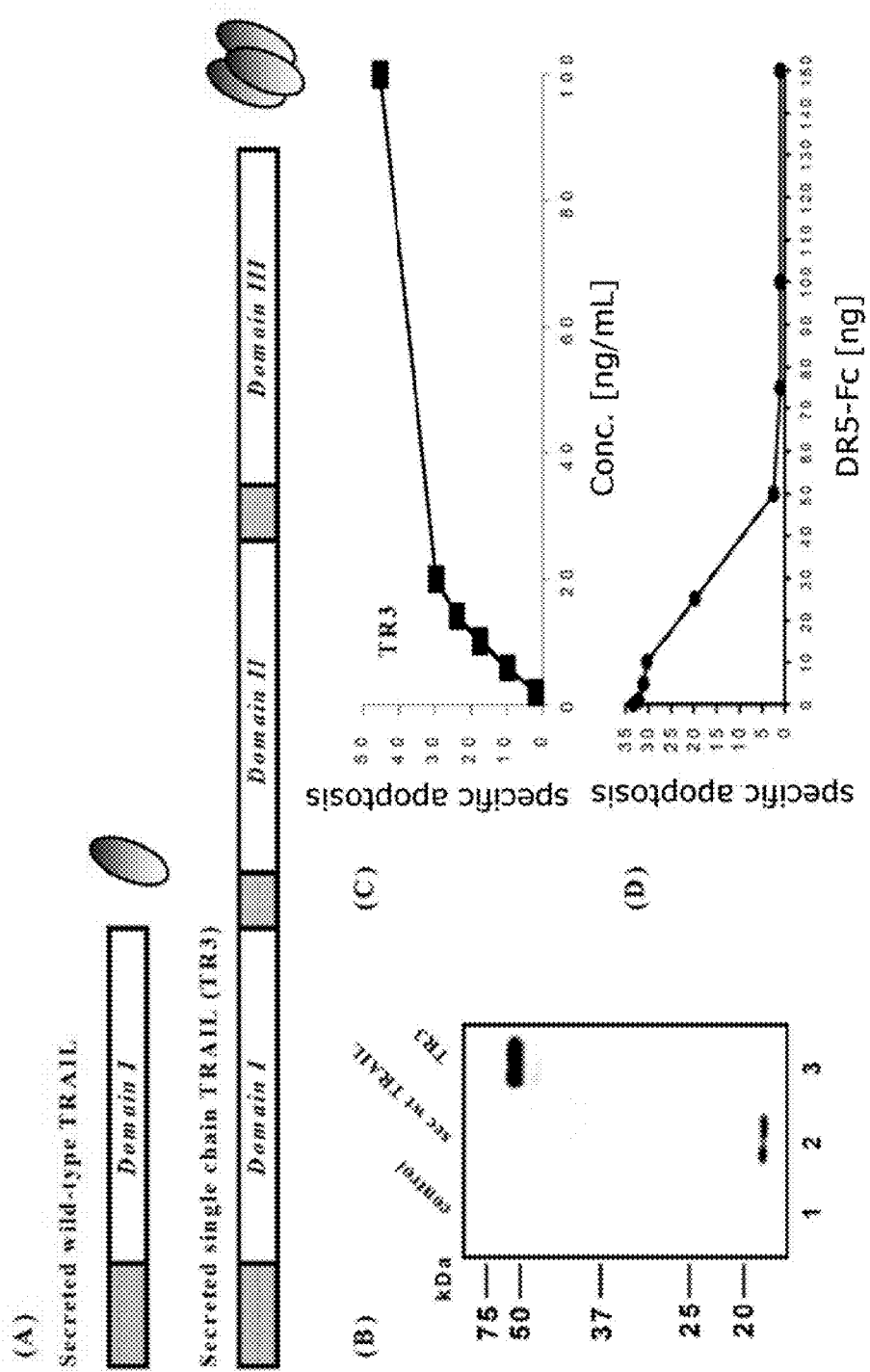
FIG. 7A illustrates a schematic representation of recombinant TR3.
FIG. 7B illustrates a Western blot analysis of commercially available TRAIL and TR3.
FIG. 7C illustrates the dose-dependent killing capacity of TR3 using FACS-based apoptosis assay with human Jurkat cells.
FIG. 7D illustrates a dose-dependent blocking of TR3 activity with soluble deatl receptor 5 (DR5-Fc).

To enforce bioactive trimerization of recombinant TRAIL, the inventors developed a strategy that does not depend on the spontaneous association of individual monomers. Endogenous human TRAIL is initially synthesized as a Type-II transmembrane protein with its carboxyl (C)-terminus facing the extracellular milieu. It is subsequently cleaved at amino acid (aa) position V114 and is then released from the cell surface (aa 114-281). The majority of recombinant secreted human TRAIL forms generated to date are comprised of amino acid 114-281 or contain a slightly elongated amino (N)-terminus (aa 95-281). The recombinant, mature form of human TRAIL described here is comprised of three consecutive domains fused together containing >99% TRAIL-specific amino acid sequence: domain I (aa 91-281), II (aa 108-281), and III (aa 108-281) (FIG. 7). To achieve addition of domains II and III, a unique restriction site was introduced at the C-terminus of wild-type TRAIL. This site was reused to sequentially attach domains II and III (aa 108-281) to the monomeric TRAIL. Of note, amino acids 108-114 can be derived from the original TRAIL sequence and only two artificial amino acids can be added for each of the two fusion sites. The resulting TRAIL form was designated TR3 and contains three consecutive domains I, II and III. By providing the three monomeric entities in a single polypeptide format, association between the individual subunits can be genetically enforced. This design can result in bioactive TRAIL which can trigger the extrinsic apoptosis pathway via the cell surface receptors DR4 and/or DR5.

The recombinant proteins were obtained by standard transfection methods with human HEK293T cells as producer cells. The supernatants were harvested and used directly or concentrated employing centrifugal filter devices and stored in aliquots at −80° C. (Spitzer et al., 2005). Integrity of the fusion proteins was verified by Western blot analysis. Commercially available TRAIL (aa 114-281) exhibits a molecular weight of 18 kDa and TR3 (shown here for a representative member of the TR3-family) has a molecular weight of ~61 kDa, consistent with its calculated size (FIG. 7B). Of note, only intact fusion protein is detected indicating absence of proteolytic degradation of TR3.

Protein preparations were then tested employing in vitro killing assays using the human, TRAIL-sensitive Jurkat T cell line. Initial functional tests revealed TR3's strong apoptosis-inducing capacity (FIG. 7C). Compared to commercially available recombinant human TRAIL, referred to hereafter as rTRAIL, TR3 exhibited an identical killing characteristic, suggesting engagement of the extrinsic death pathway. To rule out the possibility that other factors might have been responsible for the killing of TRAIL-sensitive human Jurkat cells in vitro, a blocking experiment with soluble death receptor 5 was performed. Soluble DR5-Fc (generated in house from culture supernatant and purified with protein A columns) showed complete inhibition of the killing potential of TR3 in a dose-dependent fashion (FIG. 7D), similar to the inhibitory effect on rTRAIL (not shown). These results demonstrate that TR3 is a covalently linked TRAIL trimer whose biological activity is indistinguishable from rTRAIL.

Furthermore, the inventors evaluated the thermostability at physiologic temperature (37° C.) which had no impact on TR3 over a 6 hour incubation period, conditions in which rTRAIL completely lost its activity (FIG. 8A). Similarly, TR3 was subjected to 10 freeze/thaw cycles and retained 100% of its activity. In the same assay, commercially available rTRAIL (Biomol) lost >90% of its biologic activity following just one such cycle (FIG. 8B).

TRAIL is a member of the TNF superfamily and is well known for its ability to cause cancer-selective apoptosis. A number of different approaches have been utilized in the past to produce biologically active TRAIL trimers, and are all based on the expression of monomeric cDNAs. In this study, recombinant human TRAIL trimers (TR3 family) were generated based on a single polypeptide format. We showed the potent apoptosis-inducing activity of TR3, similar to rTRAIL but with an enhanced stability profile compared with the latter. We further believe that the genetic approach to trimerization will extend to other TNF family members. In fact, we found that a similar concept has been reported for TNF, and similar to TR3, recombinant TNF trimers also showed increased stability compared with their noncovalently associated form (Krippner-Heidenreich, A., et al., J. Immunol. 2008, 180:8176-8183). However, one finding of our current work is the fact that TR3 can be further genetically modified while TRAIL activity remains fully preserved. In this report, we show the feasibility of such modifications by incorporating cell-targeting epitopes to the parental TR3 molecule. As an example, we have shown that an antibody fragment (scFv) with specificity for mouse RBCs to the NH2-terminus of TR3 allowed us to deliver bioactive TRAIL to a native cell membrane in a stoichiometrically controlled fashion. This latter point represents another key feature of the TR3 platform technology and means that one targeting molecule (scFv) could deliver a prearranged, bioactive TRAIL trimer (TR3) to a defined target site. Therefore, changing the scFv fragment to one that specifically targets a cancer cell may reduce some of the off-target toxicity associated with other rTRAIL formulations (LeBlanc, et al., Cell Death Differ. 2003, 10:66-75). A similar strategy has been recently applied using a monomeric TRAIL-encoding scFv fusion construct (Ten, C. B., et al., Leukemia 2009, 23:1389-97; Bremer, E., et al., J. Mol. Med. 2008, 86:909-924; Bremer, E., et al., Int. J. Cancer 2004, 109:281-290), which generated predominantly monomeric as well as dimeric and only a minor fraction of biologically active trimeric complexes (Bremer, E., et al., Int. J. Cancer 2004, 109:281-290). Therefore, without being limited by theory, we believe that the steric control provided by our assembly strategy (scFv:TR3=1:3) expands on the size and nature of attachments to TR3 to a greater extent than we would envision to encounter by combining three TRAIL molecules, each carrying a cell targeting antibody fragment.

Another important modification we explored was the elongated spacer domain, inserted between the targeting scFv and TR3. We expected this configuration (a) to better enable binding to the RBC via scFv and (b) to elevate the TR3 domain farther away from the RBC surface, thereby better allowing an interaction with target cell-expressed death receptors. We found that, when RBC bound, this spacer substantially enhanced the activity of the drug compared with its spacer-deficient analog. The fact that such a spacer-containing TR3 molecule was capable of bridging two unrelated cell types (TR3-decorated RBCs and Jurkat/BxPC3 cells) and can induce apoptosis via cell-cell contact, indicates that other anticancer therapeutics based on this design can be as capable of bridging tumor-specific antigens and DR4/5 located on the same cell (cis-effect) as well as adjacent cells (transeffect) causing apoptosis of both tumor cells.

In addition, the nearly complete absence of artificial linker sequences of TR3 and the incorporation of spacer sequences with human origin, human DAF and CR1 domains (scFv-S-TR3), has the theoretical advantage of reducing potential immunogenicity of a novel therapeutic based on this technology.

Secreted TRAIL, expressed from a monomeric cDNA in mammalian cells, is mostly inactive (Bodmer, J. L., et al., J. Biol. Chem. 2000, 275:20632-20637). This has been attributed mainly to the formation of interchain disulfide bridges, which in turn causes this mixture of TRAIL monomers, dimers, and trimers to have reduced affinity for its cell surface receptors. We have been able to confirm these results and found that an enforced trimer formation via an isoleucine-zipper domain could restore TRAIL activity. Therefore, trimer enforcement via generation of TR3 resembles more closely an isoleucine zipper-TRAIL configuration. Without being limited by theory, formation of these disulfide bridges is likely being disabled because TR3 is biologically highly active when produced from mammalian cells. These findings can have important consequences when biochemical postproduction manipulations are not an option. One example represents gene therapy in which the patient's own (mammalian) cells are the source of the therapeutic protein. Although such a concept has been investigated (Griffith, T. S., et al., Curr. Gene Ther. 2009, 9:9-19), TR3 can be a powerful alternative over TRAIL produced from a monomer-encoding cDNA.

A potential activity-enhancing modification relates to the location where the additional fusion partners of TR3 were attached. We initiated our studies by fusing these domains to the $NH_2$-terminus of TR3. However, we have recently shown that switching the scFv from the NH2- to the COON-terminus of an RBC-targeted mouse complement regulator resulted in a substantial increase in its activity (Mongkolsapaya, J., et al., Nat. Struct. Biol. 1999, 6:1048-1053). Theoretically, those types of variations could also increase the activity of tumor-targeted TR3 variants, considering that both termini of the TR3 fusion protein should be accessible in light of several reported crystallographic studies on noncovalently associated TRAIL trimers (Mongkolsapaya, J., et al., Nat. Struct. Biol. 1999, 6:1048-1053; Hymowitz, S. G., et al., Mol. Cell 1999, 4:563-571; Cha, S. S., et al., Immunity 1999, 11:253-261; Cha, S. S., et al., J. Biol. Chem. 2000, 275:31171-31177).

Furthermore, TRAIL binding specificity can be tailored by genetic engineering (by introducing several amino acid substitutions) toward either of the two death-inducing receptors DR4 or DR5 (Kelley, R. F., et al., J. Biol. Chem. 2005, 280:2205-2212), depending on which death receptor would represent the more promising therapeutic target. These types of alterations can be applied to TR3.

One unexpected observation is that the addition of nontargeted TRAIL forms (TR3 and rTRAIL) to the Jurkat target cells consistently resulted in a plateau in killing at ~40% to 60%. This plateau effect has been considered a limitation of TRAIL-based monotherapies (Spencer, S. L., Nature 2009, 459:428-432). With TRAIL immobilized on a solid matrix (the RBC surface), this plateau was consistently overcome. Our observations indicate that there can be cell signaling advantages to a surface-based TR3 delivery platform.

EXAMPLES

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; and textbooks such as Hedrickson et al., Organic Chemistry 3rd edition, McGraw Hill, N.Y., 1970. Synthesis of tracers, including synthesis of oligopeptides, can be accomplished using routine methods well know to skilled artisans. In some cases, oligopeptides can be obtained from a commercial supplier, such as, for example, (Cys 18)-Atrial Natriuretic Factor (4-18) amide (rat; Code H-3134) from Bachem (Torrence, Calif.) Pharmaceutical methods and compositions described herein, including methods for determination of effective amounts for imaging, and terminology used to describe such methods and compositions, are well known to skilled artisans and can be adapted from standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present teachings and the appended claims, the singular forms "a", "an" and "the" are intended to include the plural forms as well, unless the context indicates otherwise.

The following examples are intended to be illustrative of various embodiments of the present teachings and are not intended to be limiting of the scope of any claim. The examples below utilize the following materials and methods. Proteins and Antibodies Recombinant human TRAIL (aa 114-281, MVRERG-PQRVAAHITGTRGRSNTLSSPN-SKNEKALGRKINSWESSRSGHSFLSNLHLRN GELVI-HEKGFYYIYSQTYFRFQEEIKENTKNDKQMVQYIYK YTSYPDPILLMKSARNSC WSKDAEYGLYSIYQG-GIFELKENDRIFVSVTNEHLIDMDHEASFFGAFLVG (SEQ ID NO:1) was purchased from Enzo Life Sciences (formerly BIOMOL International). Antihuman TRAIL polyclonal antibody (rabbit) was obtained from Peprotech. FITC-conjugated antihuman IgG was purchased from Sigma, the Annexin-V/FITC apoptosis kit was purchased from Biosource, and cell viability was determined using a luciferase-based readout (CellTiter-Glo, Promega). Construction of expression plasmids The wild-type, $NH_2$-terminal ectodomain of human TRAIL (TR) described in this study contains amino acids 91 to 281, MILRTSEET-ISTVQEKQQNISPLVRERGPQRVAAHIT-GTRGRSNTLSSPNSKNEKALGRKI NSWESSRSGHS-FLSNLHLRNGELVIHEKGFYYIYSQTYFRFQEEIKENT KNDKQMVQYIY KYTSYPDPILLMKSARN-SCWSKDAEYGLYSIYQGGIFELKEN-DRIFVSVTNEHLIDMDHE ASFFGAFLVG (SEQ ID NO: 2) domain I; compare FIG. 1A, including the striped box; the white box represents aa 114-281 of rTRAIL).

DNA

Figure 16:
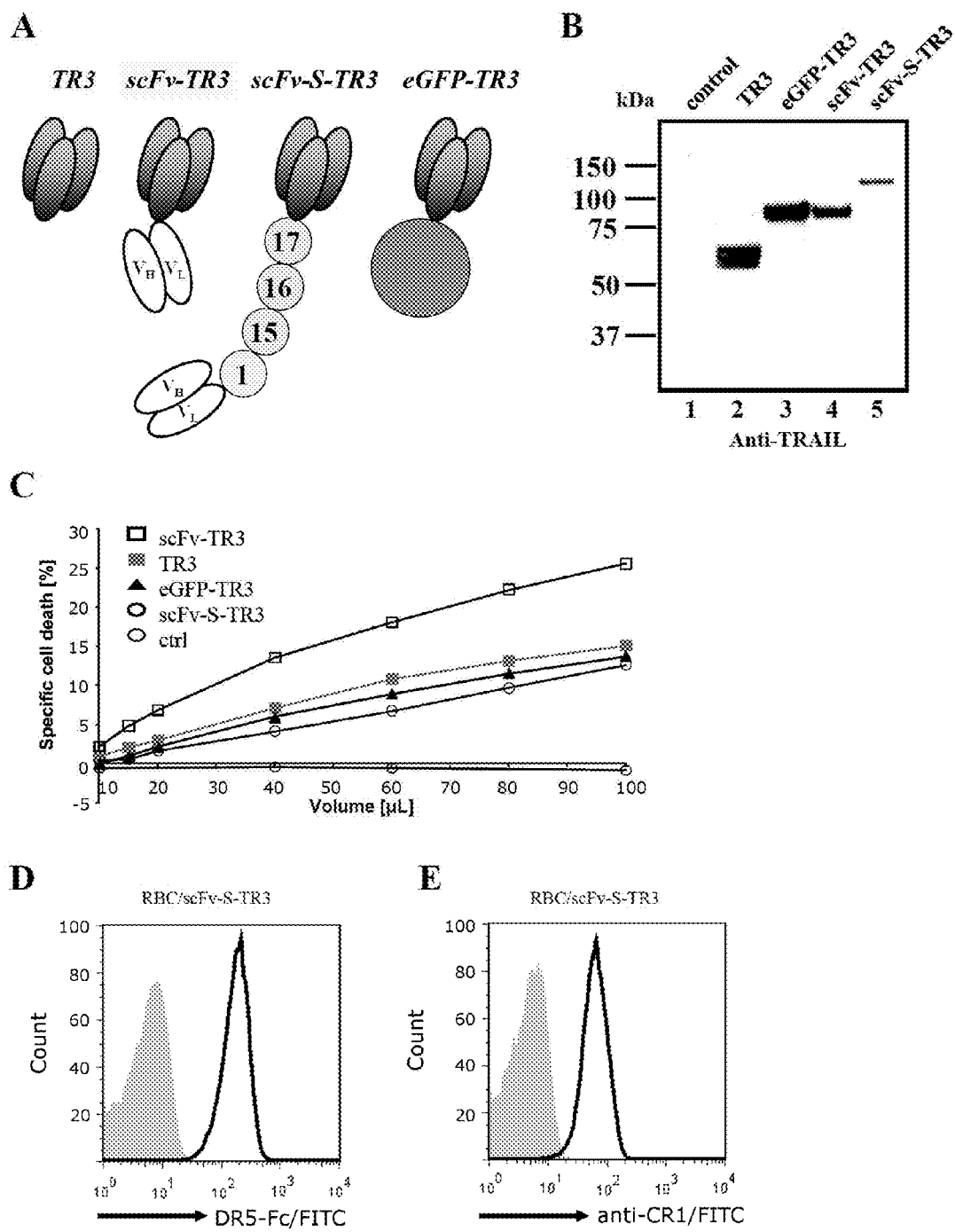
FIG. 16A illustrates a schematic representation of parental TR3, eGFP-TR3, and the two RBC-targeted TR3 forms (scFv-S-TR3 [with spacer] and scFv-TR3 [without spacer]).
FIG. 16B illustrates Western blot analysis of all fusion constructs expressed in HEK293T cells.
FIG. 16C illustrates all TR3 forms are capable of inducing apoptosis on DR5-expressing Jurkat reporter cells.
FIG. 16D illustrates mouse RBCs coated with scFv-S-TR3, washed and stained in parallel with DR5-Fc.
FIG. 16E illustrates mouse RBCs coated with scFv-S-TR3, washed and stained in parallel with anti-CR1 in mAB.

A 594 bp DNA fragment amplified by PCR from a human U937 cDNA library (Spitzer, D., et al., J. Immunol. 2007, 179: 2600-2608.) was inserted via BsiWI (5') and HindIII (3') into sT-DAF (Spitzer, D., et al., Mol. Immunol. 2004, 40: 911-919). This basic TRAIL plasmid, designated pTRBgl, contains an additional BglII site immediately upstream of TRAIL's native stop codon for subsequent cloning purposes. It also contains a sequence encoding a signal peptide to ensure secretion of the protein. Following linearization of pTRBgl with BglII and HindIII, the slightly smaller PCR-derived domains I' (5' BamHI and 3' HindIII), containing a sequence encoding amino acids 108 to 281 of native TRAIL, were added stepwise resulting in pTR2 (intermediate) and pTR3, respectively. A sequence encoding the $NH_2$-terminal enhanced green fluorescent protein (eGFP) extension of TR3 was introduced as an EcoRI/BsiWI PCR fragment into pTR3, resulting in the eGFP-TR3 fusion protein (FIG. 16A). Similarly, scFv-TR3 was generated by inserting the 735 bp BsiWI scFv Ter-119 fragment from sT-DAF into the BsiWI-linearized pTR3 plasmid. The chimera comprising the complement regulatory proteins DAF (short consensus repeat 1 (SCR1)) and CR1 (SCRs 15-17), targeted to the mouse RBC membrane via scFv Ter-119, has been described earlier (Ter-CR1, D. S. and J. P. Atkinson, unpublished data). This cDNA served as a PCR template to generate a scFv-DAF-CR1 fragment that was flanked by the restriction sites XhoI (5') and SnaBI (3'). This first fragment was then combined with a SnaBI/HindIII PCR-derived TR3 fragment and the XhoI/HindIII backbone of pSBC-1 (Dirks, W., et al., Gene 1994, 149: 387-388), resulting in the spacer-containing scFv-S-TR3 form (FIG. 16A). All PCR-derived DNA fragments were verified by DNA sequencing (Washington University Sequencing Core).

Cells, Transfections, and Protein Production

Human embryonic kidney cells (HEK293T, American Type Culture Collection (ATCC), CRL-11268) were used for protein generation. They were maintained in DMEM (Invitrogen) containing 10% FCS (Harlan). Media were supplemented with L-glutamine (Sigma), nonessential amino acids (BioWhittaker), and penicillin and streptomycin (Celigro, Mediatech). The human T-cell line Jurkat (ATCC, TIB-152) and the pancreatic cancer cell line BxPC3 (ATCC, CRL-1687) were maintained in RPMI 1640 medium (Invitrogen), supplemented with 10% FCS, L-glutamine, and penicillin/streptomycin. The recombinant TR3 forms and soluble death receptor 5 (DR5-Fc, provided by Thomas Griffith, University of Iowa) were prepared by transient expression in HEK293T cells using Gibco Opti-Mem serum-free medium and TransIT-293 (Minis, MIR2700) transfection reagent, as per the manufacturer's instructions. To obtain concentrated TR3 protein stocks, the supernatants were applied to centrifugal filter devices with a 10 kDa molecular cutoff (Centricon Plus-20, Millipore). DR5-Fc was purified using Protein A columns as per the manufacturer's instructions (Pierce). Protein concentration was determined with a spectrophotometer using bovine serum albumin (New England Biolabs) as a standard.

Animals

C57BL/6 wild-type (WT) mice were used as an erythrocyte source and as recipients for recombinant TRAIL forms. Blood was collected from the tail vein using heparinized glass capillaries for coating experiments with scFv-(S)-TR3 and for the generation of plasma. Six- to eight-week-old male nude mice (nu/nu; Harlan) were used as hosts for tumor xenografts. Human BxPC3 tumor cells ($5 \times 10^5$ cells/animal) were injected s.c. into the right flanks of the mice along with 40 times of mouse RBCs [$2 \times 10^7$, effector:target (E:T) ratio=40] in a total volume of 50 µL of FCS-free culture medium. The tumor size was measured with calipers using the following formula: Volume=0.5 (length×width$^2$) (Euhus, D. M., et al., J. Surg. Oncol. 1986, 31: 229-234). Procedures involving mice were approved by the Washington University Animal Studies Committee and conducted in accordance with the guidelines for the care and use of laboratory research animals established by the NIH.

In Vitro Coating of Mouse RBCs with Targeted TR3

Several concentrations of mouse blood and TR3-containing culture supernatants were used as described in the text and figure legends. Briefly, 1 to 4 µL of mouse whole blood ($\sim 1$-$4 \times 10^7$ RBCs) were incubated with up to 1.5 mL of the filtered, HEK293T culture supernatant for 2 hours at room temperature, washed, and then processed for flow cytometry or subjected to coculture experiments with human Jurkat and BxPC3 cells. Supernatants from nontransfected HEK293T cells served as a control.

Cell Death Determinations

Figure 17:
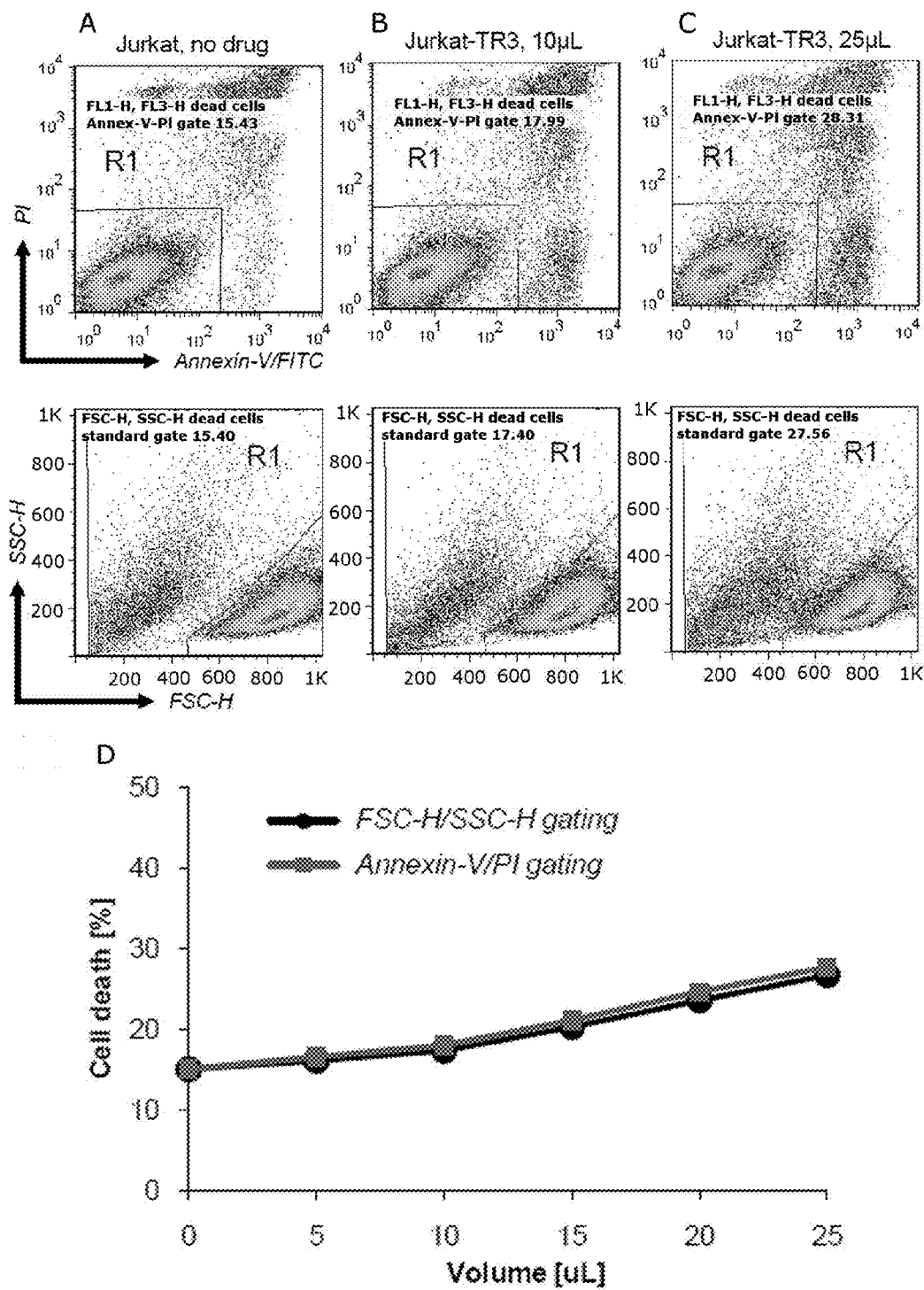
FIG. 17A illustrates a FACS-based apoptosis assay in human Jurkat cells treated with no drug.
FIG. 17B illustrates a FACS-based apoptosis assay in human Jurkat cells treated with 10 μL of TR3.
FIG. 17C illustrates a FACS-based apoptosis assay in human Jurkat cells treated with 25 μL of TR3.
FIG. 17D illustrates the validity of the FACS-based apoptosis assay in human Jurkat cells in determining cell death.
Figure 18:
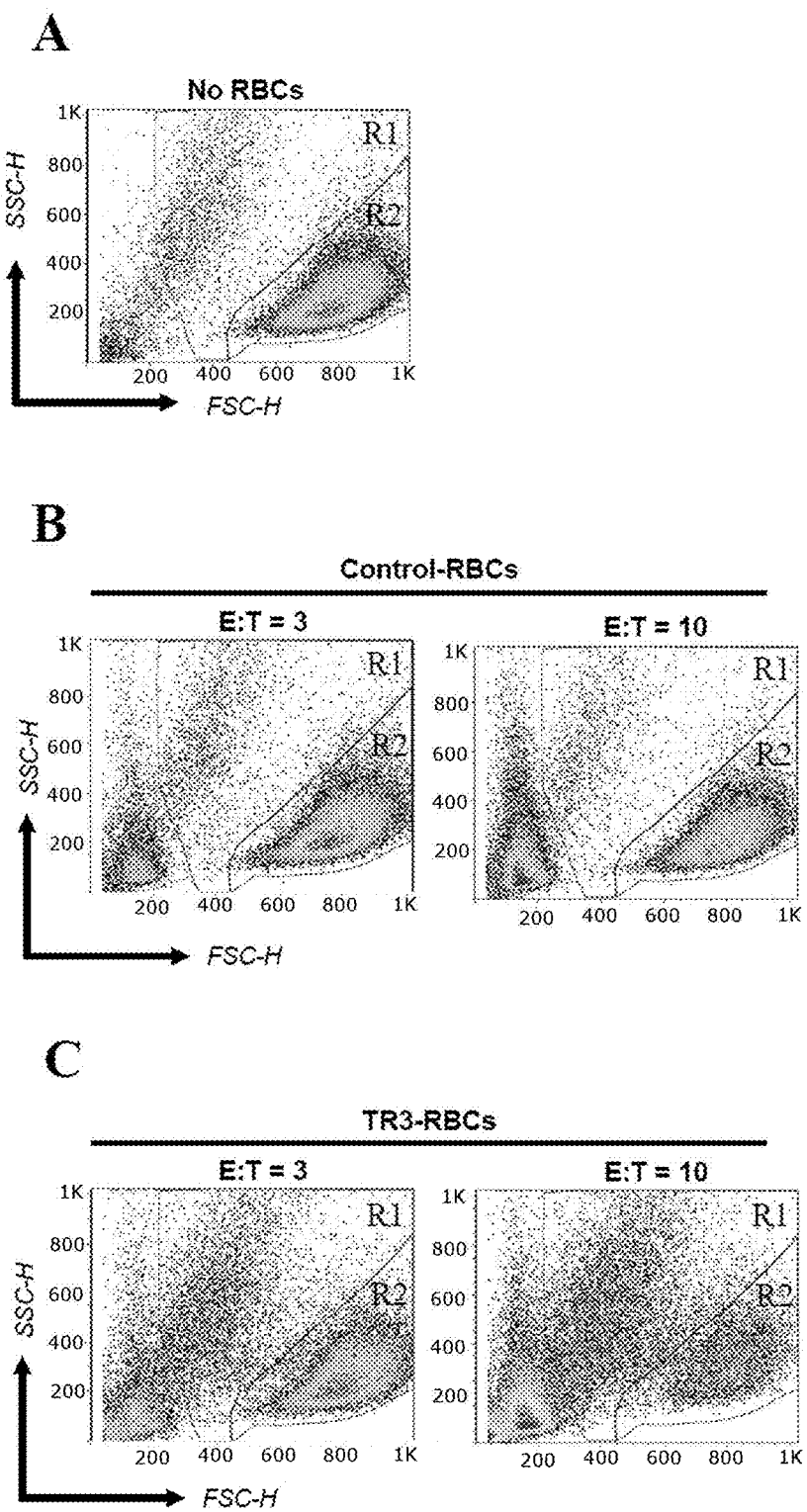
FIG. 18A illustrates the baseline situation of untreated Jurkat cells in the absence of RBCs.
FIG. 18B illustrates the addition of naive control-RBCs to the Jurkat target cells can be visualized.
FIG. 18C illustrates the addition of TR3-coated RBCs to the Jurkat target cells results in an increase in apoptotic events.

The killing capacity of our novel TR3 forms was routinely assessed employing a morphology-based FACS assay using Jurkat reporter cells. This procedure gave identical results compared with a standard Annexin-V/propidium iodide staining protocol (FIG. 17). Unless otherwise stated, the simplified protocol was employed to compare the cell killing activities of the various TRAIL forms. A FACS-based viability assay was similarly employed when RBCs were present during apoptosis measurements (FIG. 18). Data acquisition was done on a FACScan flow cytometer (Becton & Dickinson). The data were analyzed with Flow-Jo software (Version 7.2.5, Tree Star). Cell viability of adherent cells was determined by crystal violet staining after fixation with 2% paraformaldehyde and CellTiter-Glo (Promega) according to the manufacturer's instructions. Data were recorded with a luminescence plate reader (Molecular Devices, SpectraMAX-Gemini, SoftMax Version 5 software).

Statistical Analyses

Linear regression analysis of RBC-mediated Jurkat and BxPC3 cell killing was calculated using Microsoft Excel software. Tumor growth curves are expressed as means±SE. A nonparametric, one-tailed t-test was done to evaluate the statistical significance of the two curves and individual data points using GraphPad Prism (V 4.02) software.

Example 1

This example illustrates design and characterization of the genetically encoded human TRAIL trimer TR3.

The recombinant, mature form of human TRAIL described here (TR3) comprises three consecutive extracellular TRAIL domains (with >99% TRAIL-specific amino acid sequence) fused together in a head-to-tail configuration (FIG. 1A). The single-chain character of the fusion protein was verified by Western blot analysis. Under reducing conditions, commercially available recombinant TRAIL (rTRAIL, aa 114-281) exhibits a molecular weight of 18 kDa, and TR3 has a molecular weight of ~61 kDa, consistent with its calculated size (FIG. 1B).

FIG. 1A is a schematic representation of the TRAIL forms used herein, including commercially available TRAIL (rTRAIL, aa 114-281, SEQ ID NO:1), domain I fragment (TR, aa 91-281, SEQ ID NO:2), and the TR3 fusion protein. The bioactive domain of secreted TRAIL (TR) has been joined three times to result in TR3. Striped boxes in FIG. 1A represent native TRAIL sequence that is slightly smaller in domains I' (aa 108-113, QNISPL, SEQ ID NO: 3) compared with domain I (aa 91-113, MILRTSEET- ISTVQEKQQNISPL (SEQ ID NO: 4). FIG. 1B is a Western blot analysis (reducing conditions) of commercially available rTRAIL (18 kDa, lane 2) and TR3 produced by HEK293T cells (~61 kDa, lane 3). Supernatant from mock-transfected HEK293T cells served as a negative control (lane 1).

Example 2

This example illustrates cell-killing activity of TR3.

In these experiments, we treated TRAIL-sensitive human Jurkat cells with TR3 or rTRAIL. A FACS-based cell-killing assay was established that takes advantage of the morphologic changes (cell shrinkage) that are induced during apoptosis (FIG. 17). We found that this new drug candidate revealed a strong apoptosis-inducing capacity (FIG. 2A, top), nearly identical to rTRAIL (FIG. 2A, bottom).

Figure 2:
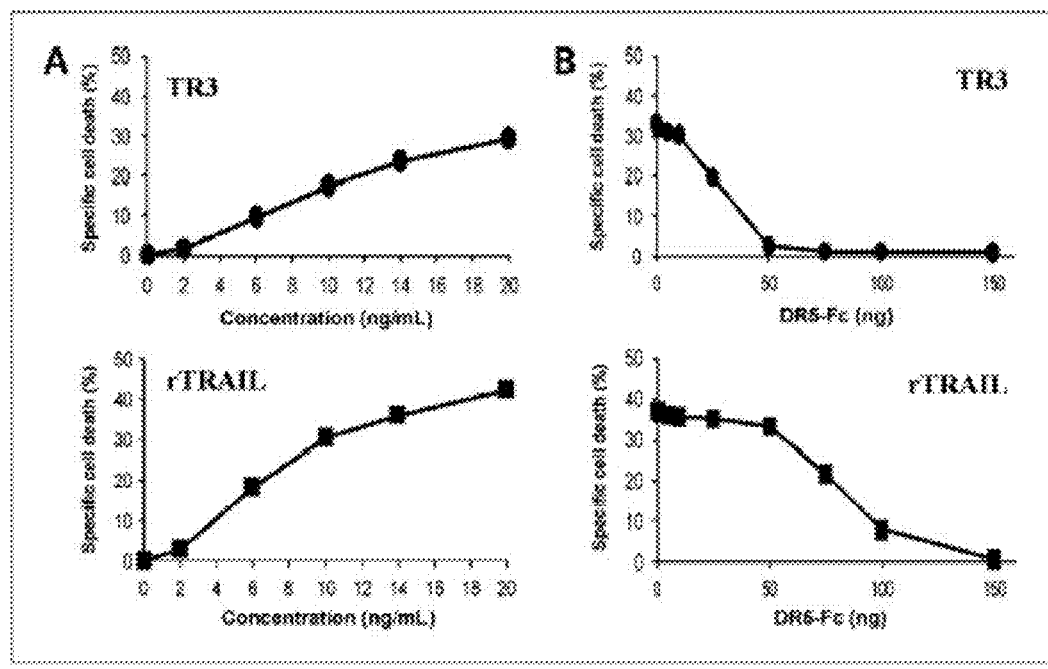
FIG. 2A illustrates the dose-dependent killing capacity of TR3 in comparison with rTRAIL using a FACS-based apoptosis assay.
FIG. 2B illustrates dose-dependent blocking of TR3 activity with soluble death receptor 5 (DR5-Fc) in comparison with rTRAIL.

As shown in FIG. 2 (see also FIG. 17), TR3 is a powerful inducer of apoptosis. FIG. 2A represents a FACS-based apoptosis assay with human Jurkat cells which shows the dose-dependent killing capacity of TR3 in comparison with rTRAIL. Protein concentration of TR3 was determined by semiquantitative Western blot analysis using known amounts of purchased rTRAIL as a reference.

Example 3

This example illustrates that the killing activity of TR3 is mediated by the death receptor pathway.

Figure 19:
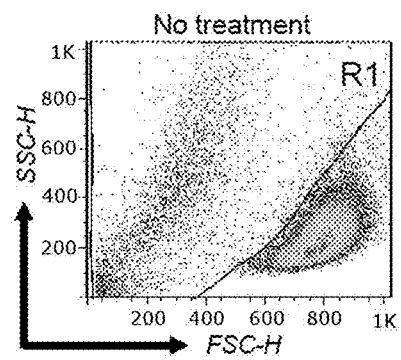
FIG. 19A illustrates the baseline situation of untreated Jurkat cells in the absence of RBCs.
FIG. 19B illustrates rTRAIL induce phenotypically identical changes in target cell morphology that are blocked with soluble DR5-Fc.
FIG. 19C illustrates TR3 induce phenotypically identical changes in target cell morphology that are blocked with soluble DR5-Fc.
Figure 19:
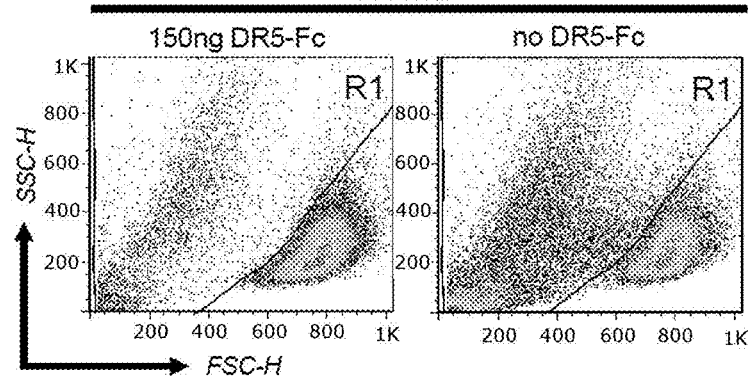
Figure 19:
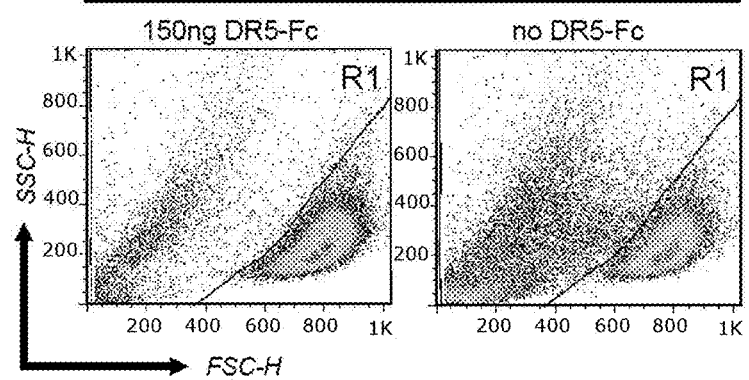

We conducted a blocking experiment employing soluble death receptor 5 (DR5-Fc) (Zhang, H-G et al., J. Virol. 2002, 76: 5692-5700). DR5-Fc reduced the killing capacity of TR3 to background levels in a dose-dependent fashion (FIG. 2B, top), similar to that of rTRAIL (FIG. 2B, bottom, and FIG. 19). FIG. 2B shows a dose-dependent blocking of TR3 activity with soluble death receptor 5 (DR5-Fc) assayed on Jurkat cells as described above for FIG. 2A. Representative dose-response curves from four replicate experiments are shown.

The faster response of TR3 to DR5-Fc solely reflects the higher starting concentration of rTRAIL chosen for this particular experiment and requires a higher dose of soluble receptor to achieve rTRAIL blockade. Without being limited by theory, this inhibition experiment suggests that TR3 assumes a native conformation, capable of interacting both with soluble DR5 and with cell-bound DR5 (the only death receptor expressed from Jurkat T cells), through which it stimulates the extrinsic death pathway and ultimately induces target cell death.

Example 4

This example illustrates unaltered specificity profile and stability of TR3.

In these experiments, we treated nontransformed, immortalized human pancreatic ductal epithelial cells with TR3 and rTRAIL. We found that both reagents did not cause cell death on these normal cells, which is consistent with the notion that TRAIL preferentially kills transformed target cells.

To assess the physicochemical properties of TR3 using defined in vitro conditions, we evaluated (a) its stability during storage at physiologic temperature and (b) the consequences of repeated freeze/thaw (F/T) cycles.

Figure 3:
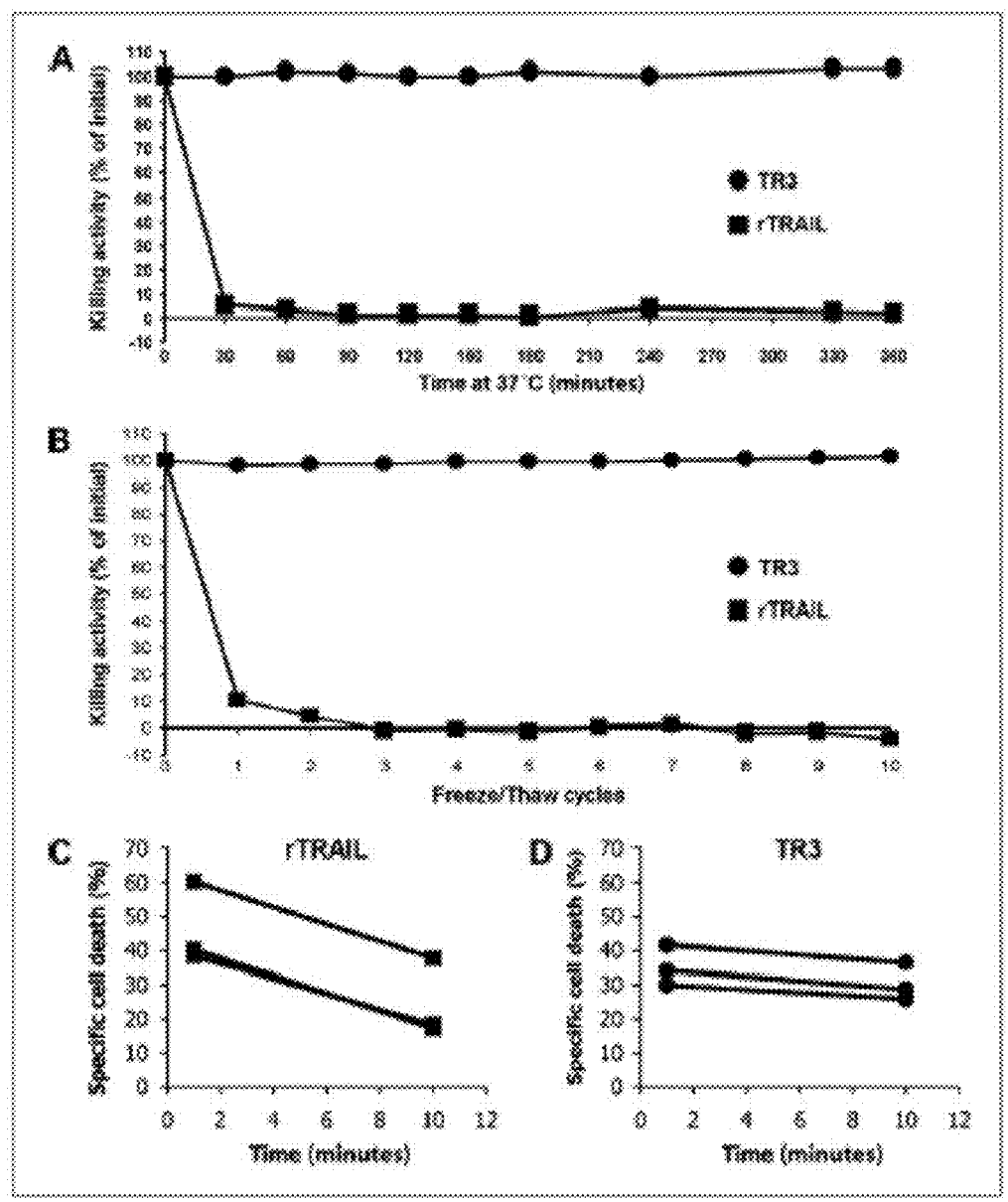
FIG. 3A illustrates killing capacity of TR3 and rTRAIL at 37° C.
FIG. 3B illustrates killing capacity of TR3 and rTRAIL following 10 freeze/thaw cycles.
FIG. 3C illustrates death-inducing activity of rTRAIL after injection into WT C57BL/6 mice.
FIG. 3D illustrates death-inducing activity of TR3 after injection into WT C57BL/6 mice.

As shown in FIG. 3A, TR3 and rTRAIL were kept at 37° C. for the indicated times. Samples were obtained and kept on ice until used in a FACS-based killing assay described for FIG. 2. When maintained at 37° C., commercially available rTRAIL readily lost a significant fraction of its initial killing potential (FIG. 3A shows >95% reduction after 30 min). In contrast, TR3 was unaffected by this treatment and retained 100% of its activity following a 6-hour incubation period at 37° C. for the indicated times (FIG. 3A). We also assessed the effect of repeated F/T cycles on the stability of TR3 compared with rTRAIL. We noted a rapid loss of activity of rTRAIL following only one F/T cycle ranging between 90% and 95% compared with the nonfrozen control (FIG. 3B). In FIG. 3B, the same killing assay as in FIG. 3A were used, but the reagents were subjected to up to 10 freeze/thaw cycles. Representative killing curves from three replicate experiments are shown. No residual killing activity was generally detected past the third F/T cycle. In contrast to rTRAIL, TR3 retained 100% of its biological activity even when cycled 10 times (FIG. 3B).

Example 5

This example illustrates that TR3 retains death-inducing activity.

In these experiments, death-inducing activity was compared between rTRAIL and TR3. In these experiments, rTRAIL (FIG. 3C) or TR3 (FIG. 3D) was injected i.v. into the tail vein of WT C57BL/6 mice and plasma was collected at the indicated time points. Death-inducing activity was then determined using Jurkat target cells as described for FIG. 3A and FIG. 3B and Example 4. Of note, the activity loss of each compound was nearly identical for each mouse (similar slope) but differed markedly between the two compounds (steeper slope for rTRAIL then for TR3).

When TR3 and rTRAIL were injected i.v. into WT C57BL/6 mice and plasma was collected and tested for biological activity at 1 minute (baseline) and 10 minutes post-injection, we found that rTRAIL lost a significant fraction of its activity within the first 10 minutes in circulation (FIG. 3C; 49.0±8.4% reduction), whereas TR3 maintained its bioactive form longer (FIG. 3D; 13.8±1.5% reduction). These results show that covalently linked TRAIL monomers (TR3) have more favorable pharmacokinetic characteristics compared to noncovalently associated rTRAIL.

Example 6

This example illustrates genetically encoded domain additions which do not interfere with TR3 function.

In these experiments, building on the increased pharmacologic stability of TR3, we addressed next how additional genetically encoded alterations (domain additions) would affect the performance of TR3. The goal of such an approach was to direct TRAIL activity more specifically to a predefined target to further increase its cell specificity and reduce its off-target effects following systemic application. Examples of an extremely functionally diverse but structurally homogeneous class of cell targeting devices are single-chain antibody fragments (scFv). Encoded by single genetic fusion sequences themselves, they are versatile entities that would allow TR3 to be targeted to a selected site and would therefore provide a secondary specificity besides the natural afficity of TRAIL for the death-inducing receptors. As a proof of concept, we introduced a scFv to the $NH_2$-terminus of TR3 that recognizes glycophorin A on the mouse RBC (scFv-TR3; FIG. 16A). This model antigen was chosen because of the lack of endogenous TRAIL receptors on the RBC membrane, and it would better facilitate our ability to interpret the results of target cell binding studies (see below). In anticipation of potential steric constraints, we designed an additional RBC-targeted TR3 form to create a larger distance between the scFv and TR3 (scFv-S-TR3; FIG. 16A). This elongated spacer comprised four SCRs, ~60 amino acid-containing globular domains of the human complement regulatory proteins decay accelerating factor (DAF, CD55) and complement receptor 1 (CR1, CD35). To show the broad applicability of our platform technology, we also added eGFP as another fusion partner of TR3 (eGFP-TR3; FIG. 16A).

FIG. 16A presents a schematic representation of parental TR3, eGFP-TR3, and the two RBC-targeted TR3 forms (scFv-S-TR3 [with spacer] and scFv-TR3 [without spacer]).

Following transient transfection of 293T cells with the respective expression plasmids, the supernatants were harvested without concentrating and used immediately to assess the relative molecular weight of each fusion protein by Western blotting (FIG. 16B, using a rabbit anti-TRAIL pAb, see also FIG. 1B) and their killing activities (FIG. 16C) employing a Jurkat-based killing assay as described in FIG. 17 and FIG. 19. The concentration process using centrifugal filter devices was omitted due to the possibility of influencing the actual concentration of the preparations. Of note, the N-terminal fusion partners have essentially no impact on the performance of the parental molecule, TR3, suggesting broad applicability of the concept. The apparent variability in killing activities (especially that of scFv-TR3) likely reflects differences in absolute protein concentrations due to DNA quality (repeated freeze/thaw cycles) among the different constructs which in turn have an impact on the transfection efficiencies. This experiment was done twice and resulted in similar killing curves. Finally, mouse RBCs were coated with scFv-S-TR3, washed and stained in parallel with DR5-Fc (FIG. 16D) and anti-CR1 mAb (FIG. 16E). Medium-treated RBCs were used as negative controls. Anti-human IgG/FITC (Sigma) and anti-mouse/FITC (Sigma) secondary antibodies were used as detection reagents. As expected, TR3 as well as the CR1 domain of the spacer region are detected with both staining reagents and give rise to a homogeneous coating pattern.

All fusion constructs were expressed in HEK293T cells and exhibited their expected molecular weights determined by Western blot analysis (scFv-TR3 at 85 kDa, scFv-S-TR3 at 110 kDa, and the eGFP-tagged TR3 at 85 kDa; FIG. 16B). To evaluate the impact of the NH2-terminal extensions of each fusion protein, the fluid-phase killing capacity of the additional TR3 variants were tested and compared with the parental molecule. Interestingly, we found that all TR3 forms were capable of inducing apoptosis on DR5-expressing Jurkat reporter cells (FIG. 16C). This result was encouraging from the perspective of designing future therapeutic drugs because we found that attachment of a 50 kDa heterologous, non-TRAIL sequence (scFv-S-TR3) did not sterically hinder the killing capacity of TR3.

Example 7

This example illustrates target cell killing with TR3-decorated RBCs in vitro.

Figure 4:
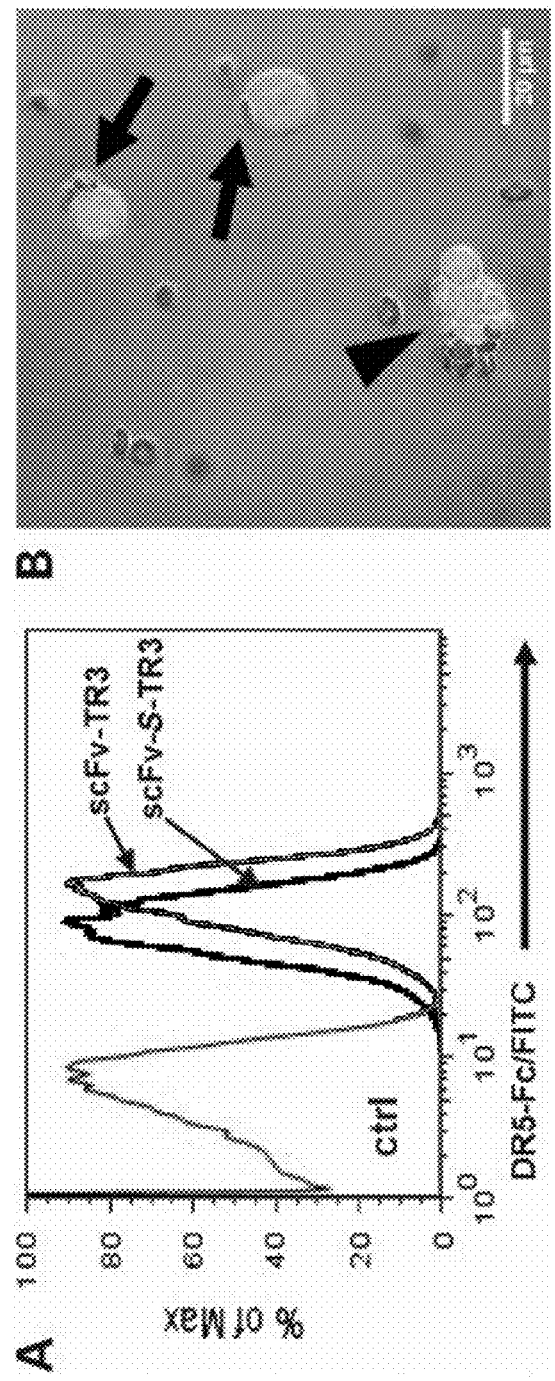
FIG. 4A illustrates presence of the fusion proteins, scFv (mR)-TR3 and scFv(mR)-S-TR3, in mouse RBCs.
FIG. 4B illustrates formation of apoptotic bodies in mouse RBCs coated scFv(mR)-S-TR3.

Although the ultimate objective was to target TR3 directly to a tumor cell membrane, we believed it was necessary to ask if scFv-TR3, and its spacer variant scFv-S-TR3, could be selectively attached to a cell membrane that lacks a TR3 binding partner. The RBC was chosen because it represents a death receptor-deficient cell type. In these experiments, the respective TRAIL forms were incubated with C57BL/6 mouse whole blood, washed, and assessed for the presence of TR3 on the RBC membranes employing purified DR5-Fc. Indeed, FACS analysis revealed a strong, homogeneous signal peak for both RBC-targeted TR3 variants (FIG. 4A). In addition, scFv-S-TR3 was also detected with an antihuman CR1 monoclonal antibody (clone 3D9), which binds to the spacer region of the fusion protein (FIG. 16D-E). The fact that a soluble DR5 receptor was capable of binding RBC-bound TR3 suggests that the death receptor-interacting domains of these large fusion proteins were folded correctly and should be also accessible by membrane-expressed DR5 on a given target cell. To prove this hypothesis, we employed a rosetting assay, in which TR3-coated murine RBCs (compare FIG. 4A for coating levels) were mixed with eYFP-expressing Jurkat target cells and were allowed to sediment at ambient temperature. We anticipated that the fusion proteins would facilitate bridging of the two cell types and consequently form aggregates (rosettes). Shortly after mixing, we identified mouse RBCs tightly attached to their green target cells (FIG. 4B, arrows). Importantly, this was true only for the spacer version of TR3 (scFv-S-TR3), because we did not observe a rosetting phenomenon in the absence of the spacer (scFv-TR3; data not shown). Moreover, once the RBCs attached to their targets, we observed programmed cell death as documented by the appearance of apoptotic bodies (FIG. 4B, arrowhead).

As shown in FIG. 4A, RBC binding of $NH_2$-terminally extended TR3 variants was verified by FACS analysis using DR5-Fc, as detected with FITC-conjugated antihuman IgG. As shown in FIG. 4B, mouse RBCs were labeled with the red membrane dye PKH-26 (Sigma) and then coated with scFv-S-TR3. They were then mixed and allowed to sediment with eYFP-expressing Jurkat cells at ambient temperature for 1 hour. Sequential images were taken with an epifluorescent microscope and then merged. This representative image shows tight binding between RBCs and Jurkat cells (arrows) and formation of apoptotic structures of the target cells (arrowhead). Original magnification, ×20.

Example 8

This example illustrates the impact of the spacer domain of scFv-S-TR3 with respect to TRAIL receptor recognition once mobilized to the RBC surface.

Figure 5:
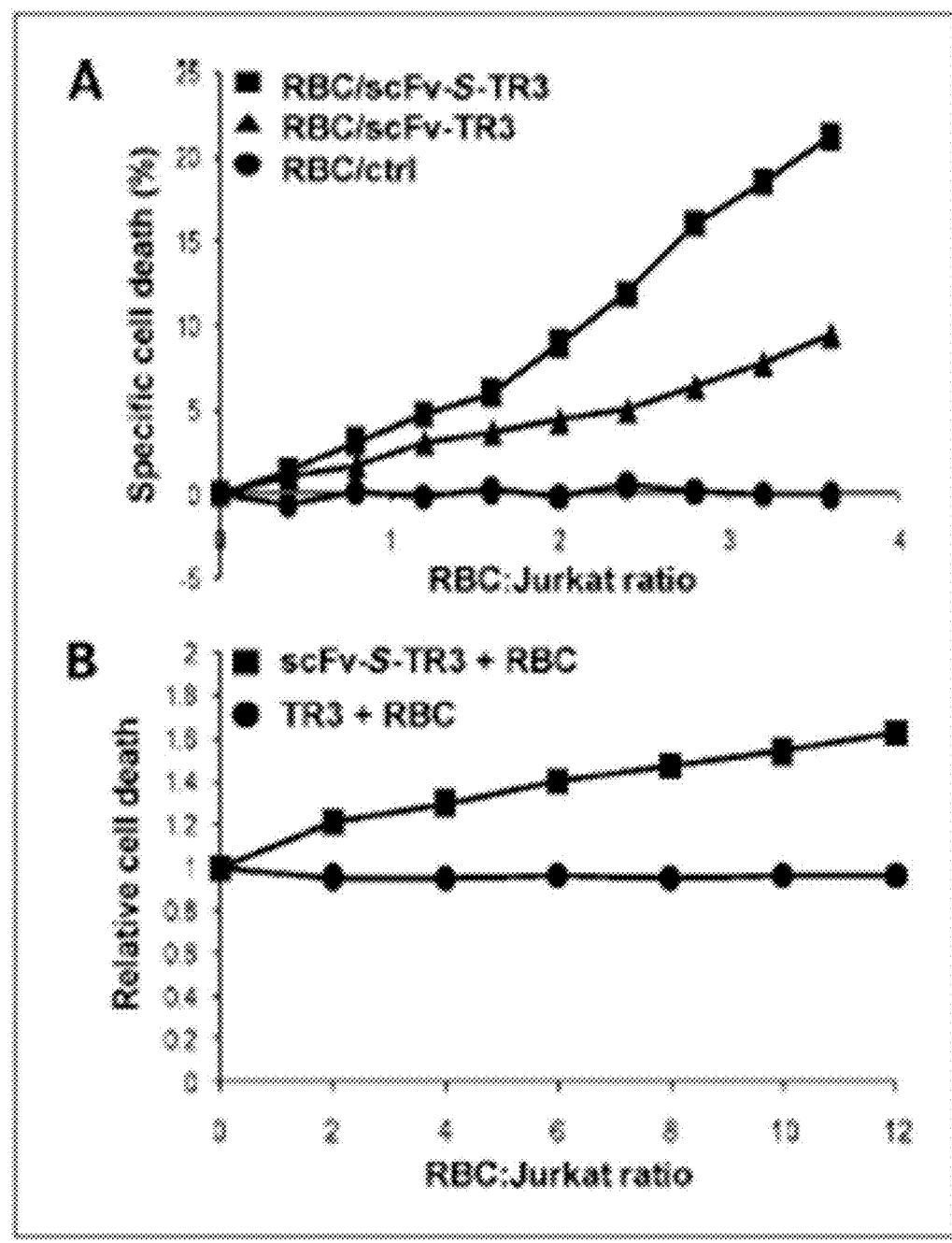
FIG. 5A illustrates RBC-targeted TR3 kills tumor cells in vitro.
FIG. 5B illustrates RBC-targeted TR3 kills tumor cells in vitro after naïve RBCs were mixed first with their Jurkat target cells at increasing ratios.

We investigated quantitatively the RBC-mediated target cell killing and study the impact of the spacer domain of scFv-S-TR3 with respect to TRAIL receptor recognition once immobilized to the RBC surface. The relative copy numbers of the RBC-bound TR3 forms were determined by DR5-Fc staining (compare FIG. 4A for TR3 coating levels). We specifically chose to attach more copies of the spacer-deficient scFv-TR3 to the RBCs because we had already shown that only the spacer variant was capable of forming rosettes, suggesting that it would likely be a more powerful inducer of target cell apoptosis. A FACS-based Jurkat killing assay in the presence of RBCs was employed similar to what has been described above (FIG. 18).

FIG. 5 shows RBC-targeted TR3 kills tumor cells in vitro. In FIG. 5A, naïve, and TR3-coated mouse RBCs (compare FIG. 4A for the respective coating levels) were cocultured at different ratios with Jurkat target cells for 24 hours and subsequently analyzed for cell viability (FIG. 19). The killing capacity of the spacer form scFv-S-TR3 is more than twice as potent (2.45-fold) although its copy number was only ~60% that of scFv-TR3 (linear regression analysis, R2=0.973 for scFv-S-TR3, and R2=0.98 for scFv-TR3). Representative killing curves from three replicate experiments are shown. FIG. 5B shows an experiment similar to the one described in FIG. 5A, but this time naïve RBCs were mixed first with their Jurkat target cells at increasing ratios. Then, a constant amount of RBC-targeted or nontargeted TR3 (control) was added to the wells and analyzed for apoptosis induction 24 hours later (baseline apoptosis 50% for both reagents in the absence of RBCs). Representative killing curves from two replicate experiments are shown. As anticipated, the presence of medium-treated control RBCs had no effect on the viability of the target cells (FIG. 5A). In contrast, we found that both RBC-targeted TR3 forms elicited cell death in this coculture system (FIG. 5A). In this comparative killing assay using only limited TR3 copy numbers attached to the RBC surface (<5,000 estimated copies/RBC), the spacer variant scFv-S-TR3 was more than twice as effective as the nonspacer form scFv-TR3 (based on the slopes of the killing curves) although we provided a much reduced copy number of the spacer variant attached to the RBC membrane (only 60% relative to scFv-TR3). It is worth mentioning that it was only possible to do these binding and killing experiments because of the improved stability of the TR3 molecule, because the coating process was done for several hours at ambient temperature, conditions under which rTRAIL would have lost its bioactivity.

To rule out that the RBC-mediated target cell killing was not induced by contaminating fluid-phase fusion proteins, we carried out a similar experiment but spatially separated effector and target cells using a transwell system. Under these conditions, target cell killing was completely abolished, confirming that TR3-decorated RBCs induce apoptosis via cell-cell contact.

In the experiments described above, we coated the RBCs prior to coculture with their Jurkat target cells. In this setting it was difficult to compare the results with regard to the exact number of TR3 molecules bound to the RBC membrane with nonbound, fluid-phase TR3. To address this issue, increasing numbers of naïve RBCs were added first to the target cells. Then, functionally equivalent doses of RBC-targeted scFv-S-TR3 and, as a control, nontargeted TR3 (with identical fluid-phase killing activities), were added to the mixtures. As expected, in the presence of non-RBC-targeted TR3, increasing numbers of RBCs did not improve (or reduce) target cell killing (FIG. 5B, killing curve remains horizontal). However, increasing concentrations of naïve RBCs during the treatment period with scFv-S-TR3 resulted in an increased target cell killing of >60% at the highest RBC concentration used, likely via in situ RBC coating (FIG. 5B). Interestingly, although the drug input was the same under these different conditions (baseline, fluid-phase killing for both drugs in the absence of RBCs ~50%), enhanced target cell killing was only possible in the presence of a "native" solid matrix, i.e., the RBC membrane. Together, these results demonstrate a method of decorating, via single-chain antibody fragments, a tumor cell surface with biologically active TR3 that can augment the native killing capacity of TRAIL while decreasing systemic toxicity.

Example 9

This example illustrates target cell killing with TR3-decorated RBCs reduces tumor growth.

Figure 6:
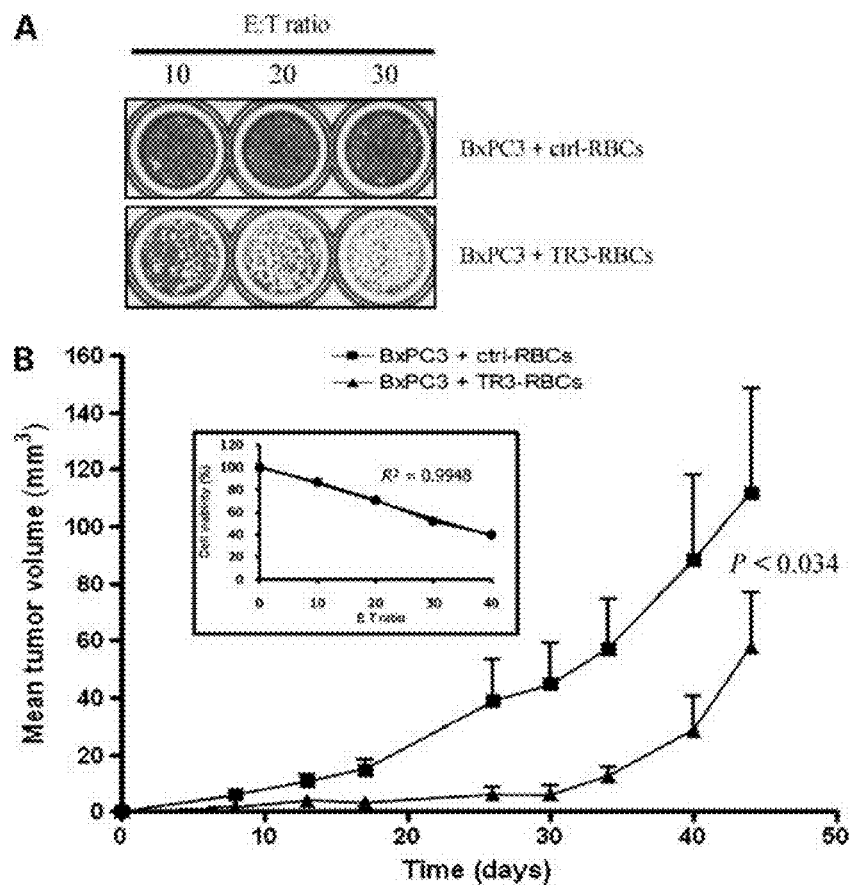
FIG. 6A illustrates in vitro killing of the pancreatic cancer cell line BxPC3 with TR3-RBCs.
FIG. 6B illustrates delayed tumor progression in mice injected with BxPC3 cells mixed with TR3-coated RBCs (scFv-S-TR3).

In these experiments, we employed a murine xenotransplantation model of pancreatic cancer to assess the ability of RBC-targeted TR3 to kill human tumor cells. FIG. 6 illustrates that human pancreatic cancer cells are killed in vivo following coinjection with TR3-coated RBCs.

In these experiments, we first confirmed the previously reported TRAIL sensitivity of BxPC3 cells by cocultivation with TR3-decorated mouse RBCs in a similar tissue culture system described above for the Jurkat T-cell line. FIG. 6A illustrates in vitro killing of the pancreatic cancer cell line BxPC3 with TR3-RBCs. A similar experiment as described for FIG. 5A in which the Jurkat cells were replaced with BxPC3 cells.

Following a nonenzymatic cell detachment procedure (PBS/EDTA), the target cells were mixed at the indicated E:T ratios with naïve and scFv-S-TR3-coated mouse RBCs. The mixtures were then cocultured for 24 hours and the cell viability was determined after fixation with 2% paraformaldehyde using crystal violet. We found that BxPC3 cells were killed by TR3-coated RBCs in a dose-dependent fashion (FIG. 6A).

To assess the killing capacity of TR3-decorated RBCs, we had to ensure that effector and target cells would have access to each other. As presented in FIG. 6B, BxPC3 cells were mixed with TR3-coated RBCs (scFv-S-TR3) at an E:T ratio of 40 immediately prior to s.c. injection into the flanks of nude mice. Medium-treated RBCs served as controls. A luminescent cell viability assay was employed in parallel to verify the killing capacity of the RBC preparation (inset). Tumor size was monitored by caliper measurements at the indicated time points and is expressed as means±SE. Each group, n=5; P<0.034 (unpaired t-test).

In these experiments, BxPC3 cells were mixed on ice (to prevent immediate rosette formation) with scFv-S-TR3-coated mouse effector RBCs at an effector:target (E:T) ratio of 40 (with $5 \times 10^5$ target cells/animal) and immediately injected into the right flanks of male nude mice. It was expected that in this particular model, at an E:T of 40, a similar fraction of the tumor targets would be eliminated (~60%; FIG. 6B, inset) within the first 24 hours after implantation due to direct and required cell contact with TR3-coated RBCs. We expected that the surviving cells (~40%) would engraft and eventually contribute to tumor formation. This is indeed what we observed. Eight days postinoculation, the control animals developed measurable tumor masses that continued to grow exponentially (FIG. 6B). In contrast, mice that received a mixture of BxPC3 and TR3-coated RBC effector cells presented with a ~30-day delay in tumor progression, after which the growth characteristics were identical to the tumors in the control animals.

Example 10

This example illustrates that single chain TRAIL (TR3) is a powerful inducer of apoptosis.

FIG. 7A presents a schematic representation of recombinant TR3. The functionally critical domain of secreted wild-type TRAIL has been joined three times by genetic engineering. FIG. 7B shows a Western blot analysis of commercially available TRAIL (lane 2, Biomol) and TR3 (lane 3). The samples were run on a 12% SDS-PAG under reducing conditions. The membrane was probed with a rabbit polyclonal Ab. Immunoreactive fragments were detected using anti-rabbit-HRP conjugated secondary Ab. Note that TR3 is fully intact without the presence of proteolytic degradation products. FIG. 7C shows a FACS-based apoptosis assay with human Jurkat cells demonstrates the dose-dependent killing capacity of TR3. Protein concentration of TR3 was determined by semiquantitative Western blot analysis using known amounts of purchased TRAIL shown in (B) to establish a standard curve (not shown). FIG. 7D presents a dose-dependent blocking of TR3 activity with soluble death receptor 5 (DR5-Fc) assayed on Jurkat cells as described in FIG. 7C.

The recombinant, mature form of human TRAIL described here is comprised of three consecutive domains fused together containing >99% TRAIL-specific amino acid sequence: domain I (aa 91-281), II (aa 108-281), and III (aa 108-281) (FIG. 7A). To achieve addition of domains II and III, a unique restriction site was introduced at the C-terminus of wild-type TRAIL. This site was reused to sequentially attach domains II and III (aa 108-281) to the monomeric TRAIL. Of note, amino acids 108-114 are derived from the original TRAIL sequence and only two artificial amino acids are added for each of the two fusion sites. The resulting TRAIL form was designated TR3 and contains three consecutive domains I, II and III. By providing the three monomeric entities in a single polypeptide format, association between the individual subunits is genetically enforced. This design resulted in bioactive TRAIL which triggered the extrinsic apoptosis pathway via the cell surface receptors DR4 and/or DR5.

The recombinant proteins were obtained by standard transfection methods with human HEK293T cells as producer cells. The supernatants were harvested and used directly or concentrated employing centrifugal filter devices and stored in aliquots at −80° C. (Spitzer, D., et al., J. Immunol. 2005, 175:7763-7770, 2005). Integrity of the fusion proteins was verified by Western blot analysis. Commercially available TRAIL (aa 114-281) exhibits a molecular weight of 18 kDa and TR3 (shown here for a representative member of the TR3-family) has a molecular weight of ~61 kDa, consistent with its calculated size (FIG. 7B). Of note, only intact fusion protein is detected indicating absence of proteolytic degradation of TR3.

Protein preparations were then tested employing in vitro killing assays using the human, TRAIL-sensitive Jurkat T cell line. Initial functional tests revealed TR3's strong apoptosis-inducing capacity (FIG. 7C). Compared to commercially available recombinant human TRAIL, referred to hereafter as rTRAIL, TR3 exhibited an identical killing characteristic, suggesting engagement of the extrinsic death pathway. To rule out the possibility that other factors might have been responsible for the killing of TRAIL-sensitive human Jurkat cells in vitro, a blocking experiment with soluble death receptor 5 was performed. Soluble DR5-Fc (generated in house from culture supernatant and purified with protein A columns) showed complete inhibition of the killing potential of TR3 in a dose-dependent fashion (FIG. 7D), similar to the inhibitory effect on rTRAIL (not shown). These results demonstrate that TR3 is a covalently linked TRAIL trimer whose biological activity is indistinguishable from rTRAIL.

Example 11

This example illustrates that TR3 is unaffected by physiologic temperature conditions and repeated freeze/thaw cycles.

In these experiments, we evaluated the thermostability at physiologic temperature (37° C.) which had no impact on TR3 over a 6 hour incubation period, conditions in which rTRAIL completely lost its activity (FIG. 8A). Similarly, TR3 was subjected to 10 freeze/thaw cycles and retained 100% of its activity. In the same assay, commercially available rTRAIL (Biomol) lost >90% of its biologic activity following just one such cycle (FIG. 8B).

As shown in FIG. 8A, TR3 (squares) and rTRAIL (circles) with a baseline killing capacity of 38% and 18%, respectively, were kept at 37° C. for the indicated time points. Samples were obtained and kept on ice until used for the killing assay employing Jurkat reporter cells. FIG. 8B: As in FIG. 8A but the reagents were subjected to up to 10 freeze/thaw cycles. TR3 (squares) and rTRAIL (circles) were allowed to freeze on dry ice for 5 min, followed by a thawing process at ambient temperature at which time point a sample was obtained that was then stored on ice until used for the killing assay.

Example 12

This example illustrates the influence on its killing capacity of additional protein domains fused to the N-terminus of TR3.

Figure 9:
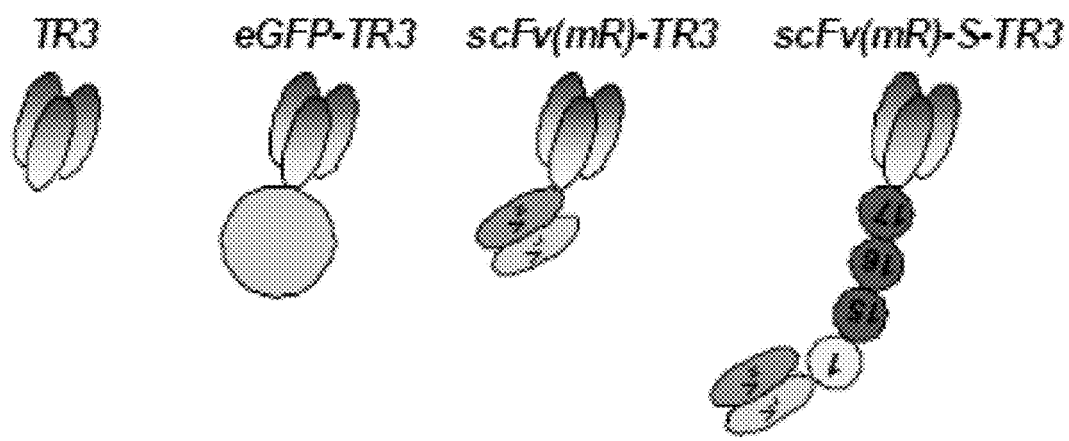
FIG. 9 illustrates a schematic of N-terminal extension variants of TR3 with tumor (antigen) targeting capabilities.

FIG. 9 presents a schematic of N-terminal extension variants of TR3 with tumor (antigen) targeting capabilities, including a cartoon of modified TR3 molecules with high molecular weight fusion partners such as eGFP and single chain Ab fragments (scFv). Shown here is a targeting scFv with specificity for a mouse red cell antigen (mR). However, scFvs can be interchanged without interfering with the TR3 function. Shown also is the spacer form (S) that contains protein domains from human DAF (SCR1) and CR1 (SCRs 15-17).

To study the influence on its killing capacity of additional protein domains fused to the N-terminus of TR3, the following constructs were generated using standard techniques: eGFP-TR3, scFv(mR)-TR3 (with specificity for glycophorin A on mouse RBCs), and a spacer variant in which four so called short consensus repeats (SCRs), ~60 amino acids-containing globular domains of the human complement regulatory proteins decay accelerating factor (DAF, CD55) and complement receptor 1 (CR1, CD35) were inserted between the scFv and TR3 to address potential steric complications (scFv(mR)-S-TR3, FIG. 9). All these TR3 fusion proteins were analyzed for integrity by immunoblotting and exhibited their respective molecular weights: eGFP-TR3 and scFv (mR)-TR3: ~81 kDa; scFv(mR)-S-TR3: ~110 kDa, data not shown).

Example 13

This example illustrates that RBC-targeted TR3 binds to and kills TRAIL receptor-positive Jurkat cells in vitro.

Figure 10:
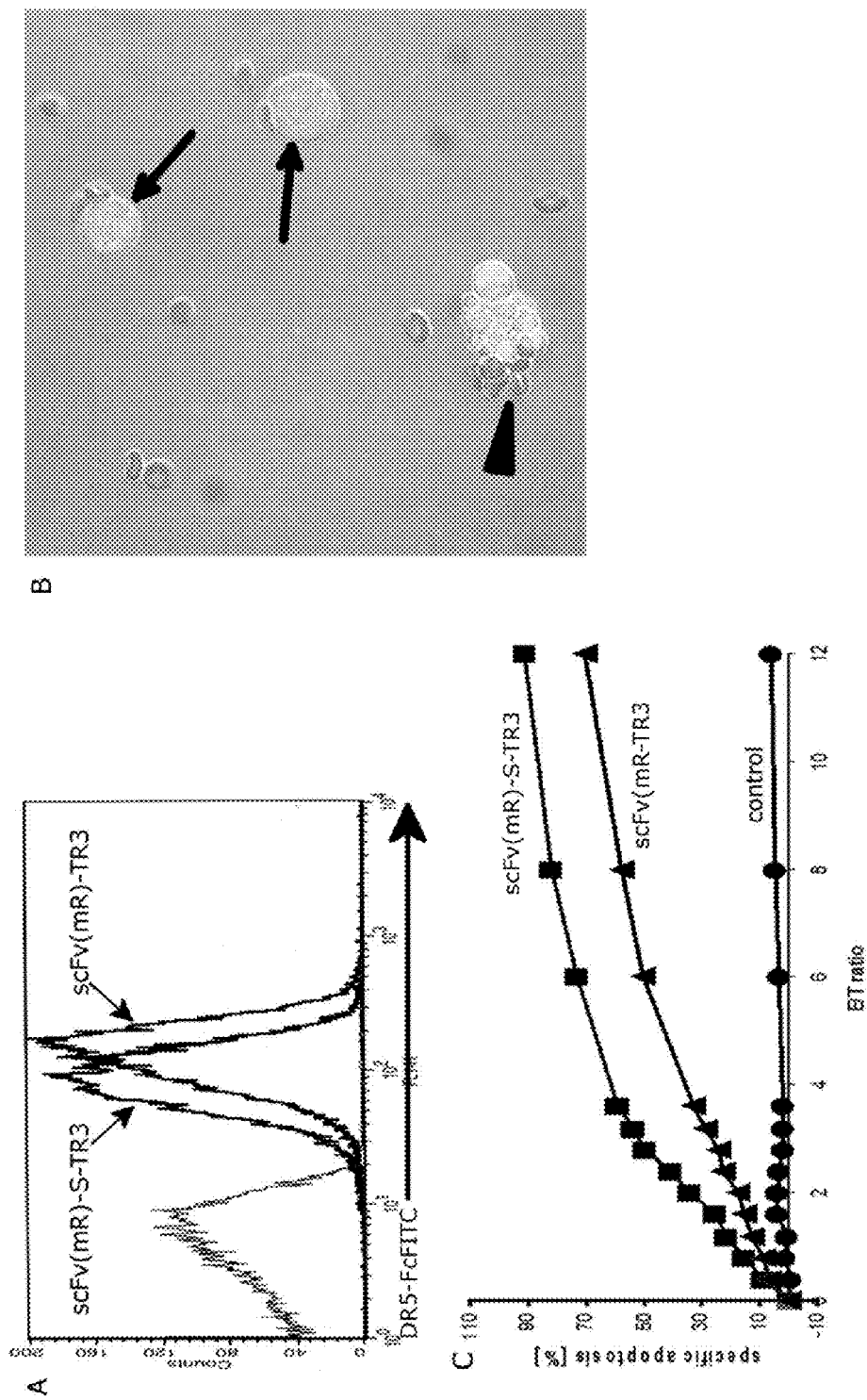
FIG. 10A illustrates presence of the fusion proteins, scFv (mR)-TR3 and scFv(mR)-S-TR3, in mouse RBCs.
FIG. 10B illustrates formation of apoptotic bodies in mouse RBCs coated with scFv(mR)-S-TR3.
FIG. 10C illustrates efficient killing capacity of their Jurkat targets after coculture of RBCs.

In these experiments, we explored the efficiency of tumor cell killing in vitro focusing on the RBC-targeted TR3 constructs. Our studies indicate that TR3 tethered onto a cell surface retains its ability to kill TRAIL-sensitive cells. To show this we have done the following experiments. First, we demonstrated binding of scFv(mR)-TR3 and scFv(mR)-S-TR3 to mouse RBCs (FIG. 4A, FIG. 10A). Second, we showed by fluorescent microscopy that RBC-bound TR3 facilitated tight binding to TRAIL receptor-positive Jurkat cells in vitro (FIG. 4B, FIG. 10B). However, only the spacer variant scFv(mR)-S-TR3 was capable of bridging the two cell types (rosette forming). And third, target cell binding by the RBCs was accompanied with a strong potential to induce killing of the Jurkat cells evident by the formation of apoptotic bodies (FIG. 4B, FIG. 10B, arrowhead), with the spacer variant being more than twice as potent as the spacer-deficient reagent (FIG. 10C). Importantly, RBC-bound TR3 demonstrates a significant increase in biologic activity compared to rTRAIL. Whereas rTRAIL exhibits a plateau in its biologic activity, killing 30-40% of tumor cells in culture, RBC-bound TR3 is able to kill >90% of tumor cells in vitro.

As shown in FIG. 4A, FIG. 10A, mouse RBCs were coated with scFv(mR)-TR3 and scFv(mR)-S-TR3. Presence of the fusion proteins was verified by DR5-Fc and FACS analysis. In FIG. 4B, FIG. 10B, mouse RBCs, labelled with the red membrane dye (PKH-26) and coated with scFv(mR)-S-TR3 were able to tightly attach to their green target cells (arrows) and also induced cell death (arrowhead). FIG. 10C shows coculture of the RBCs shown in FIG. 10A and demonstrates efficient killing capacity of their Jurkat targets. Note that the copy number of scFv(mR)-S-TR3 (squares) is only 65% that of scFv(mR)-TR3 (triangles). Medium-treated RBCs were used as control (circles).

Example 14

This example illustrates that RBC-targeted TR3 binds to and kills TRAIL receptor-positive human pancreatic cancer cells BxPC3 in vitro.

Figure 11:
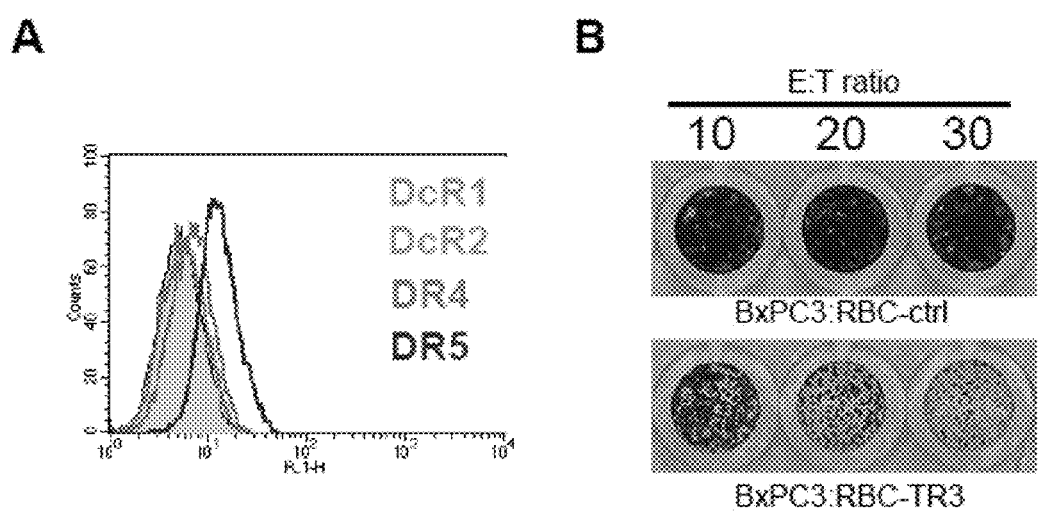
FIG. 11A illustrates death receptor expression profile of human BxPC3 cells as determined by FACS analysis.
FIG. 11B illustrates mouse RBCS, coated with scFv(mR)-S-TR3 are capable of killing BxPC3 cells in vitro.

We studied the effect of RBC-immobilized TR3 on BxPC3 cell killing in vitro. This human pancreatic cancer cell line is known to be TRAIL-sensitive (Ashkenazi, A., et al., J. Clin. Oncol. 2008, 26:3621-3630; Mori, T., et al., J. Surg. Res. 2007, 142:281-286.) and primarily expresses DR5, the major apoptosis-inducing receptor (FIG. 11A). Following non-enzymatic harvesting of these adherent cells (to prevent alteration of its death receptor status), the cells were cocultivated with mouse RBCs precoated with scFv(mR)-S-TR3 using the indicated effector:target (E:T) ratios. In agreement with the results obtained with human Jurkat cellsRBC-associated TR3 (FIG. 11B).

FIG. 11A shows death receptor expression profile of human BxPC3 cells as determined by FACS analysis. These cells primarily express the activating death receptor DR5. FIG. 11B shows that mouse RBCs, coated with scFv(mR)-S-TR3 are capable of killing BxPC3 cells in vitro. In these experiments, $1 \times 10^5$ cancer cells were cocultured for two days with up to $3 \times 10^6$ RBCs (effector:target (E:T) ratio=30) in a 96-well format. After fixing the cells with paraformaldehyde, the surviving cells were stained with crystal violet. All of the cells treated with TRAIL-negative control RBCs survived and formed a confluent monolayer (upper panel), while >90% of the cells were killed at an E:T of 30 (lower panel).

These experiments demonstrate the principle that the biologic activity of TRAIL can be extended by fusion constructs such as TR3 and the variants described above. These studies helped us identify the most potent candidate (the spacer variant scFv(mR)-S-TR3) to move forward to the next level of TR3-based drug development. The high degree of structural similarity amongst scFv molecules (in analogy to mAbs of the same isotype, which only differ in their complementarity determining regions (CDRs)), the regions of an antibody that define to what antigen it will bind), make these entities uniquely suitable to be interchanged. This structural similarity is therefore unlikely to alter the biologic functions of TRAIL (TR3), once replaced by one that recognizes mesothelin (or a different specificity).

Example 15

To establish the validity of our approach as well as to select pancreas tumor cell lines for in vivo study, we demonstrated that TRAIL-sensitive pancreas cancer cell lines overexpress the tumor marker mesothelin on their cell surface. It has been recently shown that a large number of human pancreatic tumor cell lines and primary patient material overexpress mesothelin on the cell surface, while it is nearly absent on normal tissues (Li, M., et al., Mol. Cancer Ther. 2008, 7:286-296). We measured the surface abundance of mesothelin on different pancreas tumor cell lines by flow cytometry and demonstrated that these cells do indeed express mesothelin (data shown for BxPC3 and CFPAC, FIG. 12).

Figure 12:
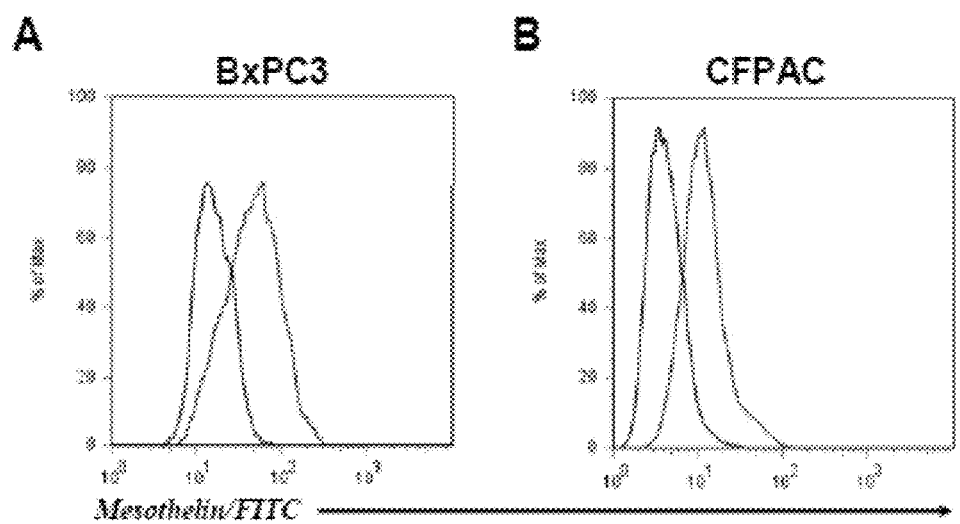
FIG. 12A illustrates human pancreatic cancer cells, BxPC3, express the tumor marker Mesothelin.
FIG. 12B illustrates human pancreatic cancer cells, CFPAC express the tumor marker Mesothelin.

FIG. 12 illustrates that human pancreatic cancer cells express the tumor marker Mesothelin. In these experiments, two human pancreatic cancer cell lines, BxPC3 (FIG. 12A), and CFPAC (FIG. 12B) were analyzed by FACS analysis to determine their mesothelin expression profiles.

Example 16

This example illustrates that scFv-SS has affinity for human Mesothelin.

In these experiments, we transfected an expression plasmid for just this protein (pING-hMeso) into Mesothelin-negative 293T cells. We then incubated the target cells with 293T-derived supernatant containing scFv(hM-L)-hDAF, a secreted form of human DAF (FIG. 13A and Spitzer, D., et al., Mol. Immunol. 2004, 40:911-919). These transiently transfected 293T-Meso cells, incubated with medium alone, served as a negative control and show the expected baseline DAF reactivity when stained with an anti-human DAF mAb (FIG. 13B). However, the very same cell preparation exhibited a strong increase in DAF signal intensity with supernatant containing scFv-(hM-L)-DAF (FIG. 13B). We conclude from these results that the scFv-SS does indeed have specificity for human Mesothelin and can deliver additional copies, in this case human DAF, to Mesothelin-positive target cells. We can therefore build on these results and replace the scFv(mR) in both RBC-targeted constructs with scFv(hM-L and -H) (see, e.g., FIG. 15).

Figure 13:
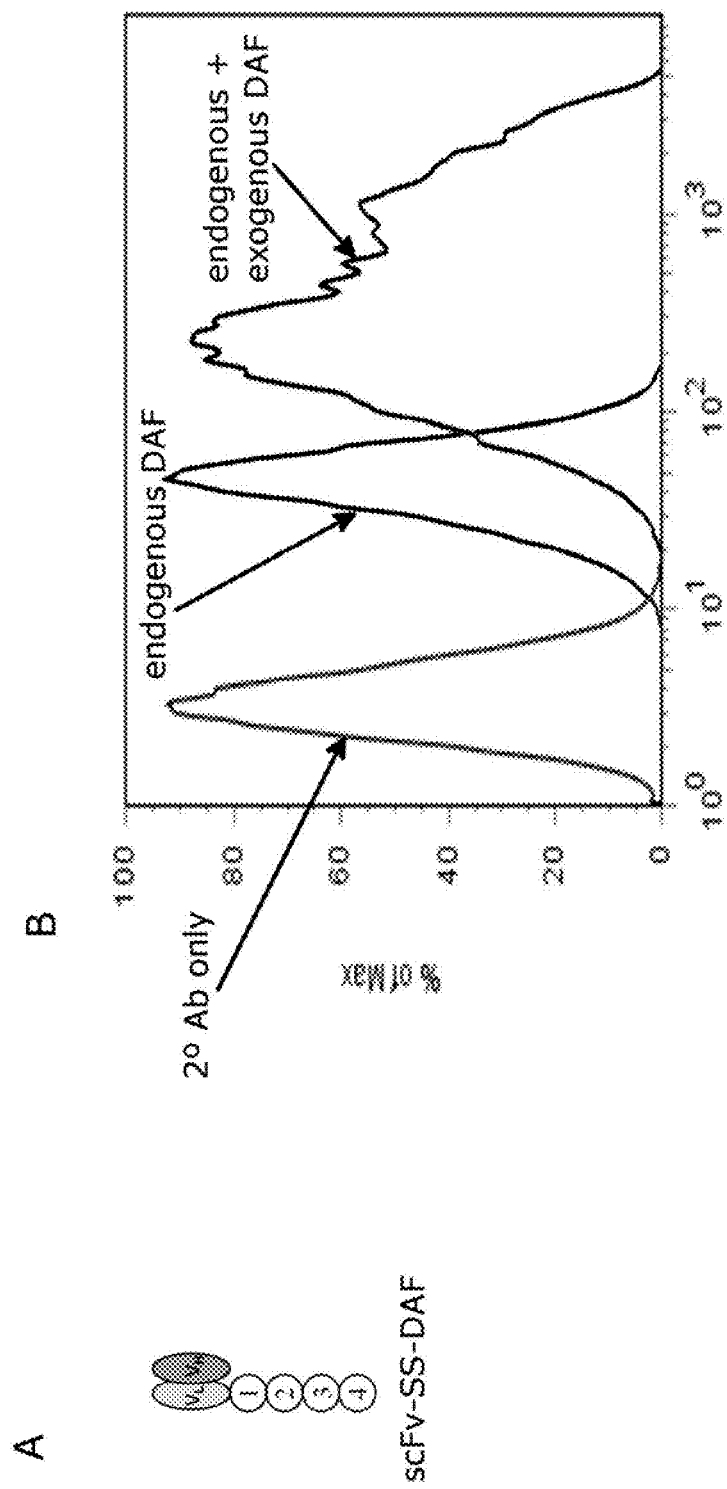
FIG. 13A illustrates a schematic of scFv(hM-L)-hDAF, a secreted form of human DAF.
FIG. 13B illustrates ScFv-SS facilitates targeting of human DAF to surface-expressed human Mesothelin.

FIG. 13 shows that ScFv-SS facilitates targeting of human DAF to surface-expressed human Mesothelin. 293T cells were transfected with a full length human Mesothelin expression plasmid. ScFv-SS with specificity for human Mesothelin was fused to a secreted human DAF form and expressed from 293T cells. The Mesothelin-expressing 293T cells were then incubated with supernatant containing scFv(hM-L)-hDAF (FIG. 13A). Medium-treated cells were used as control. The cells were next washed and assessed for presence of DAF with a monoclonal Ab against human DAF and subjected to FACS analysis (FIG. 13B). Labels indicate secondary Ab only, endogenous DAF level, and endogenous plus exogenous DAF attached to the target cells via Mesothelin binding.

Example 17

Figure 14:
FIG. 14 illustrates strategic sites within the TR3 protein for the insertion of additional small functional entities.

This example illustrates strategic sites within the TR3 protein for the insertion of additional small functional entities (FIG. 14). Arrows indicate four potential sites at which an epitope tag (6×His) could be inserted to obtain purified TR3 protein. As an example, a central site is highlighted by an arrow between junction II and III of the molecule.

Example 18

This example illustrates molecular design of TR3 targeted to human Mesothelin.

Antibodies and scFvs are known to exhibit varying affinities for a given antigen. We are able to study anti-human Mesothelin scFvs with High and Low affinity (H and L). As described above (FIG. 13), we already verified the binding capacity of scFv-SS toward human Mesothelin. This scFv has been described (Chowdhury, P. S., et al., Proc. Natl. Acad. Sci. USA 1998, 95:669-674) and represents a low affinity antibody fragment [scFv(hM-L)], which can be increased by somatic hypermutation in vitro (Chowdhury and Pastan, Nat. Biotechnol. 1999, 17:568-572) (FIG. 15, right panel). In this study, the authors identified two amino acid substitutions within the scFv-SS sequence (CDR-L3) that led to a 15-fold increase in binding affinity over the parental antibody fragment, designated scFv-SS1, corresponding to scFv(hM-H)

(FIG. 15, left panel). These two substitutions are located at positions 93/94 in which a Gly/Tyr motive is replaced by a Lys/His sequence. These alterations can be introduced by standard methods (site-directed mutagenesis) and the impact of the increased binding affinity of the targeting domain can be studied on Mesothelin-positive BxPC3 cells in vitro.

FIG. 15 illustrates mesothelin-targeted TR3 forms. Molecular design of TR3 targeted to human Mesothelin. Two sets of similar reagents are shown that only differ in their binding affinity for the tumor marker. The two low-affinity TR3 forms are shown on the right (scFv(hM-L)-TR3 and scFv(hM-L)-S-TR3), the high-affinity forms are shown on the left (scFv(hM-H)-TR3 and scFv(hM-H)-S-TR3).

Example 19

This example illustrates Biochemical characterization of TR3 variants containing various high molecular weight N-terminal extensions (FIG. 16). FIG. 16A depicts a schematic representation of parental TR3, eGFP-TR3, and the two RBC-targeted TR3 forms (scFv-S-TR3 [with spacer] and scFv-TR3 [without spacer]). Following transient transfection of 293T cells with the respective expression plasmids, the supernatants were harvested without concentrating and used immediately to assess the relative molecular weight of each fusion protein by Western blotting (FIG. 16B, using a rabbit anti-TRAIL pAb, see also FIG. 1B). Their killing activities were also assessed (FIG. 16C) employing a Jurkat-based killing assay as described per FIG. 17 and FIG. 19. The concentration process using centrifugal filter devices was omitted due to the possibility of influencing the actual concentration of the preparations. Of note, the N-terminal fusion partners have essentially no impact on the performance of the parental molecule, TR3, suggesting broad applicability of the concept. The apparent variability in killing activities (especially that of scFv-TR3) likely reflects differences in absolute protein concentrations due to DNA quality (repeated freeze/thaw cycles) among the different constructs which in turn have an impact on the transfection efficiencies. This experiment was done twice and resulted in similar killing curves. Finally, mouse RBCs were coated with scFv-S-TR3, washed and stained in parallel with DR5-Fc (FIG. 16D) and anti-CR1 mAb (FIG. 16E). Medium-treated RBCs were used as negative controls. Anti-human IgG/FITC (Sigma) and anti-mouse/FITC (Sigma) secondary antibodies were used as detection reagents. As expected, TR3 as well as the CR1 domain of the spacer region are detected with both staining reagents and give rise to a homogeneous coating pattern.

Example 20

This example illustrates assessment of TR3 biological activity by comparing a morphology-based apoptosis assay with an Annexin-V/PI staining protocol.

In order to determine the killing capacity of our novel TR3 forms, we employed a simple and reliable FACS-based apoptosis assay. One of the key morphological features that change during programmed cell death is cell shrinkage (reduction in forward scatter [FSC] values). This phenomenon can be easily monitored by flow cytometry. For this assay, the live cell population was moved for all measurements to the far and lower right of the dot plot to account for the expected shift of the cells to the left (shrinkage) during apoptosis (FIG. 17A-C lower panels). Percent dead cells are found in gate R1. Specific apoptosis was calculated by subtracting the percent baseline apoptosis of untreated control cells (FIG. 17A, lower panel). This simplified protocol was then compared with a standard Annexin-V-FITC (FL1-H)/PI (FL3-H) staining procedure (FIG. 17A-C, upper panels). Percent dead cells can be found in R1 and include early apoptotic, late apoptotic and necrotic cells. Specific apoptosis was calculated by subtracting the percent baseline apoptosis of untreated control cells (FIG. 17A, upper panel). Both protocols resulted in essentially the same result (FIG. 17D, curves represent mean data points performed in duplicates) establishing the validity of the simplified method that was used hereafter for determining Jurkat target cell death. For each measurement, a total of $6\times10^4$ events were recorded.

Example 21

This example illustrates a modified morphology-based apoptosis assay in the presence of mouse RBCs.

FIG. 18 depicts a similar setup as described for FIG. 17 and FIG. 19 (below) in the absence of RBCs during apoptosis measurements. However, due to their small size, the RBCs accumulate in the lower left corner of the dot plot. To exclude the RBCs from the calculations, the area of gate R1 was slightly reduced, without significantly impacting the outcome of the results. Another gate R2 was created to quantify the live cell population. Percent apoptosis was calculated with the following formula: % R1/(% R1+% R2)×100. Specific apoptosis was calculated similarly but the percent baseline apoptosis was subtracted. FIG. 18A: Baseline situation of untreated Jurkat cells in the absence of RBCs. The addition of naive control-RBCs to the Jurkat target cells can be visualized in the lower left corner using a low (FIG. 18B, left panel, E:T=3) and a higher RBC concentration (FIG. 18B, right panel, E:T=10). In contrast, addition of TR3-coated RBCs to the Jurkat target cells results in an increase in events in R1 and, consequently in a reduction in R2, which translates to an increase in apoptosis at a low (FIG. 18C, left panel, E:T=3) and high RBC concentration (FIG. 18C, right panel, E:T=10). These raw data represent the basis for the graphs presented in FIG. 5.

Example 22

This example illustrates that TR3 and rTRAIL induce phenotypically identical changes in target cell morphology that are blocked with soluble DR5-Fc.

In these experiments, comparable amounts of rTRAIL (B) and TR3 (FIG. 19C) were added to the Jurkat cells in the presence of increasing concentrations of DR5-Fc (shown here is only the highest dose). The same morphology-based apoptosis assay was employed to assess the ability of DR5-Fc to block cell death as described for FIG. 17 (A-C, lower panels). Percent dead cells are found in gate R1. Specific apoptosis was calculated by subtracting the percent baseline apoptosis of untreated control cells (FIG. 19A). Representative dot plots are shown. Of note, compared to rTRA TR3-treated Jurkat cells undergo identical phenotypical changes (dot plot patterns) suggesting that TR3 assumes a conformation identical to the native homotrimer.

What is claimed is:

1. A trimer of a TNF-related apoptosis-inducing ligand (TRAIL), comprising:

three consecutive extracellular TRAIL domains fused together in a head-to-tail configuration;

a cell-targeting domain; and a spacer between the cell-targeting domain and the TRAIL domains, wherein the spacer comprises globular domains of human complement regulatory proteins decay accelerating factor (DAF, CD55) and/or complement receptor 1 (CR1, CD35).

2. A trimer in accordance with claim 1, wherein the spacer comprises four SCRs.

* * * * *